United States Patent
Yoon et al.

(10) Patent No.: US 11,938,236 B2
(45) Date of Patent: Mar. 26, 2024

(54) MEDICAL DRESSING

(71) Applicant: SEOUL VIOSYS CO., LTD., Gyeonggi-do (KR)

(72) Inventors: Yeong Min Yoon, Gyeonggi-do (KR); Hee Ho Bae, Gyeonggi-do (KR); A Young Lee, Gyeonggi-do (KR); Hyun-Suk Suh, Seoul (KR); Joon-Pio Hong, Seoul (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 921 days.

(21) Appl. No.: 16/542,573

(22) Filed: Aug. 16, 2019

(65) Prior Publication Data

US 2020/0078482 A1    Mar. 12, 2020

Related U.S. Application Data

(60) Provisional application No. 62/825,993, filed on Mar. 29, 2019, provisional application No. 62/764,960, (Continued)

(51) Int. Cl.
*A61L 2/10* (2006.01)
*A61F 13/00* (2006.01)

(52) U.S. Cl.
CPC .......... *A61L 2/10* (2013.01); *A61F 13/00068* (2013.01); *A61F 2013/00174* (2013.01); *A61F 2013/0091* (2013.01)

(58) Field of Classification Search
CPC ........ A61F 13/00068; A61F 2013/0091; A61F 2013/00174; A61F 7/00; A61F 7/007; A61F 2007/0001; A61F 2007/00187; A61L 2/10; A61L 2/0047; A61N 2005/0651; A61N 5/0624

(Continued)

(56) References Cited

U.S. PATENT DOCUMENTS

2010/0161009 A1  6/2010  Forster
2011/0288617 A1  11/2011  Sharma
(Continued)

FOREIGN PATENT DOCUMENTS

JP   2014-524754 A   9/2014
JP   2017-504560 A   2/2017
(Continued)

OTHER PUBLICATIONS

Extended European Search Report issued in corresponding EP Application No. 19849174.8, dated May 19, 2022, 7 pages.
(Continued)

*Primary Examiner* — Tarla R Patel
(74) *Attorney, Agent, or Firm* — Perkins Coie LLP

(57) ABSTRACT

A dressing is used for curing a wound, and includes a dressing body having a first plane to make contact with a wound of a patient and a second plane opposite to the first surface, a display unit provided on the second plane to display information, and having a flexibility, and a light irradiation device to apply light the wound of the patient. The light irradiation device includes a device board, at least one light emitting diode mounted on the device board, and a water-proof protective film provided on the light emitting diode to protect the light emitting diode.

20 Claims, 27 Drawing Sheets

Related U.S. Application Data filed on Aug. 17, 2018, provisional application No. 62/764,962, filed on Aug. 17, 2018.

(58) Field of Classification Search
USPC .................................................. 602/2
See application file for complete search history.

(56) References Cited

U.S. PATENT DOCUMENTS

| | | |
|---|---|---|
| 2012/0165716 A1 | 6/2012 | Reuben |
| 2012/0265120 A1* | 10/2012 | Beisang, III ......... A61N 5/0624 |
| | | 604/20 |
| 2014/0066868 A1 | 3/2014 | Freedman et al. |
| 2016/0015962 A1 | 1/2016 | Mehdi et al. |
| 2016/0114067 A1* | 4/2016 | Dobrinsky ................ A61L 2/10 |
| | | 250/461.1 |
| 2016/0271280 A1* | 9/2016 | Liao ....................... G06F 3/0393 |
| 2018/0056087 A1* | 3/2018 | Ribeiro .................... A61L 15/00 |
| 2020/0289330 A1* | 9/2020 | Spector ................ A61N 5/0624 |
| 2021/0001001 A1* | 1/2021 | Das ......................... C08L 83/06 |

FOREIGN PATENT DOCUMENTS

| | | |
|---|---|---|
| KR | 10-0935711 B1 | 1/2010 |
| KR | 10-2015-0014819 A | 2/2015 |
| WO | 2013066694 A2 | 5/2013 |

OTHER PUBLICATIONS

International Search Report for Application No. PCT/KR2019/010499 dated Nov. 25, 2019, 4 pages.

* cited by examiner

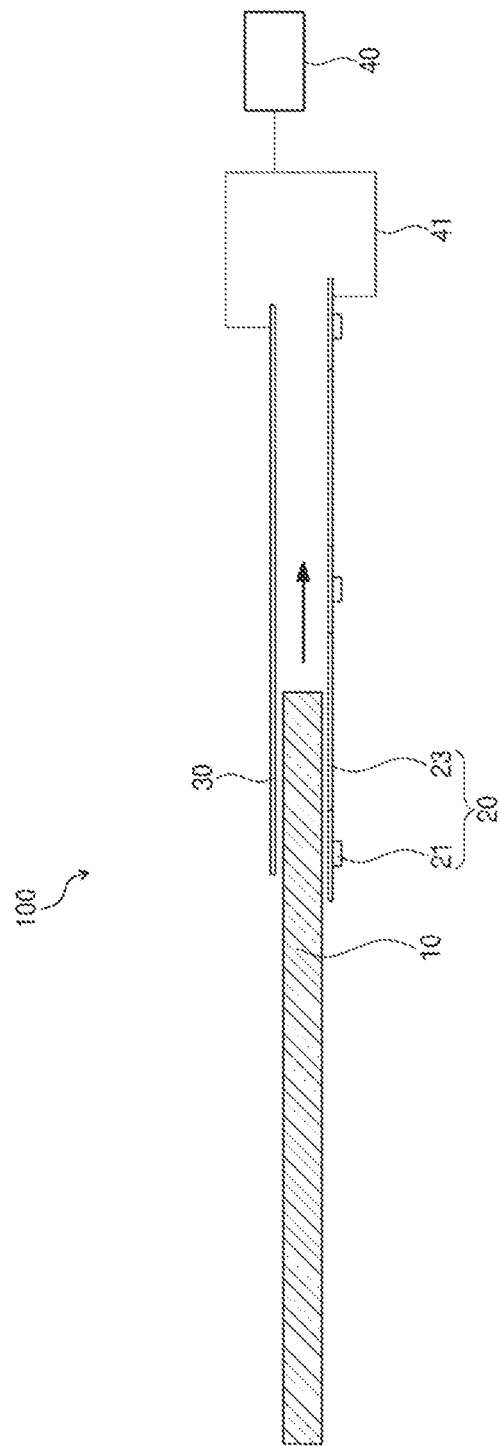

MEDICAL DRESSING

CROSS-REFERENCE TO RELATED APPLICATIONS

This application claims the benefit of U.S. Provisional Application No. 62/764,960, filed on Aug. 17, 2018, No. 62/764,962, filed on Aug. 17, 2018, and No. 62/825,993, filed on Mar. 29, 2019, which are hereby incorporated by reference for all purposes as if fully set forth herein.

BACKGROUND

Embodiments of the present disclosure described herein relate to a light irradiation device and, more particularly, to a dressing for curing a wound.

When a human or an animal is wounded, the wound is cured through an infection phase of producing a large amount of exudate, a proliferation phase that granulation formation is actually started, and a maturation phase in which neonatal skin is made robust. The most important thing in the curing process is to rapidly absorb exudate to minimize the infection phase, and to maintain a proper wetting environment. To this end, various types of dressing materials have been developed.

SUMMARY

Embodiments of the present disclosure are directed to providing a dressing having higher sterilization and infection inhibition effects.

In one embodiment of the present disclosure, the dressing is applied to a wound of a patient. The dressing includes a dressing body to make contact with the wound of the patient and a light irradiation device to apply light to the wound of the patent for sterilization and infection inhibition. The light has a wavelength band, which is to induce destruction of bacteria present in the wound of the patient or to accelerate a recovery of the wound, among an infrared light wavelength, a visible light wavelength, and an ultraviolet light wavelength.

According to an embodiment of the present disclosure, the light irradiation device may include first and second light sources to emit first light and second light at timings close to each other, regardless of whether the timings overlap or not, the first light and the second light having mutually different wavelength bands. The first light may be light having a wavelength band for inducing the destruction of the bacteria by damaging a cell as the first light acts on a photosensitizer present in the bacteria, and the second light may be a light having a wavelength band for inducing the destruction of the bacteria by changing the structure of a genetic material present in the cell of the bacteria.

According to an embodiment of the present disclosure, the first light may be blue light, and the second light is ultraviolet light, and the second light may be irradiated with a daily maximum irradiation amount of about 3 mJ/cm$^2$.

According to an embodiment of the present disclosure, the first light may have a wavelength in a range of about 400 nm to about 420 nm or a range of about 455 nm to about 470 nm.

According to an embodiment of the present disclosure, the dressing may further include a controller to control the first light and the second light.

According to an embodiment of the present disclosure, the dressing may further include an oxygenator connected with the controller to supply oxygen.

According to an embodiment of the present disclosure, the first light is irradiated for a first time, and the second light is irradiated for a second time shorter than the first time.

According to an embodiment of the present disclosure, the second light is started to be irradiated after the first light is completely irradiated.

According to an embodiment of the present disclosure, the second light is started to be irradiated before the irradiation of the first light is completed, and at least a portion of the first time and the second time has a mutually overlapping duration.

According to an embodiment of the present disclosure, the dressing body may have a first surface to make contact with the wound of the patient and a second surface opposite to the first surface, and the light irradiation device may include a device board, at least one light emitting diode mounted on the device board; and a water-proof protective film provided on the light emitting diode to protect the light emitting diode.

According to an embodiment of the present disclosure, the dressing may further include a drape provided in the dressing body and attached to a skin close to the wound of the patient to form an inner surface by covering the wound, a negative pressure generating member to apply negative pressure to the inner space by communicating with the inner space, and a tube to connect the inner space with the negative pressure generating member.

According to an embodiment of the present disclosure, the dressing may further include a pressure sensor provided in the inner space to sense whether the negative pressure is applied to the inner space, and the pressure sensor may be provided on the device board.

According to an embodiment of the present disclosure, the dressing body may have a first thickness when the negative pressure is applied, and has a second thickness when the negative pressure is applied, and the light emitting diode may be exposed from the device board toward the wound to correspond to the second thickness when the negative pressure is applied.

According to an embodiment of the present disclosure, the dressing body may have an exudate opening to absorb the exudate from the wound.

According to an embodiment of the present disclosure, the light emitting diode may be provided in a form of a flip chip having first and second electrodes, and the first and second electrodes of the flip chip may be directly connected with a wiring of the device board.

According to an embodiment of the present disclosure, the dressing body may be at least one of a foam dressing type, a hydrocolloid dressing type, a porous silicone film dressing type, or a hydrofiber dressing type.

According to an embodiment of the present disclosure, the dressing may further include a sensor unit provided inside or outside the dressing body to sense a state of the wound of the patient.

According to an embodiment of the present disclosure, the light irradiation device may interwork with the sensor unit to set a wavelength and an output intensity of light emitted from the light emitting diode.

According to an embodiment of the present disclosure, the light irradiation device may emit light having a wavelength band varied depending on a phase of the wound of the patient.

According to an embodiment of the present disclosure, the light irradiation device may emit light having a blue wavelength band, when the phase of the wound of the patient is an infection phase, emit light having green wavelength band or red wavelength band, when the phase of the wound of the patient is a proliferation phase, or emit light having red wavelength band or infrared wavelength band, when the phase of the wound of the patient is a maturation phase.

BRIEF DESCRIPTION OF THE FIGURES

The above and other objects and features of the present disclosure will become apparent by describing in detail exemplary embodiments thereof with reference to the accompanying drawings.

FIG. 11 is a cross-sectional view illustrating a dressing according to an embodiment of the present disclosure.

FIGS. 35A and 35B are photographs obtained by capturing images of the shape of the wound area based on days, in which FIG. 35A is a photograph of wounds in a non-irradiation group, and FIG. 35B is a photograph of wounds in the light irradiation group;

FIG. 37 is a view illustrating sterilization power measured as a function of a light amount depending on the presence of oxygen.

DETAILED DESCRIPTION OF EMBODIMENTS

Figure 1:
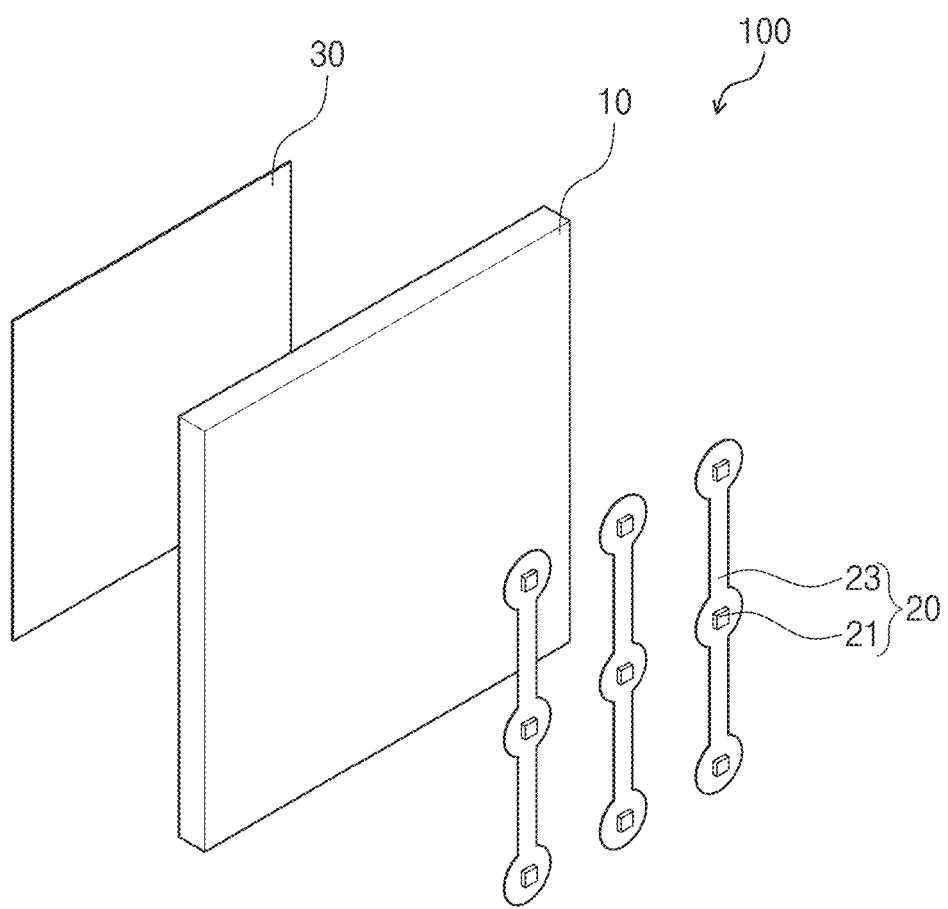
FIG. 1 is an exploded perspective view illustrating a dressing according to an embodiment of the present disclosure.

While the present disclosure is susceptible to various modifications and alternative forms, specific embodiments thereof are shown by way of example in the drawings and will be described herein in detail. It should be understood, however, that there is no intent to limit the present disclosure to the particular forms disclosed, but on the contrary, the present disclosure is to cover all modifications, equivalents, and alternatives falling within the spirit and scope of the present disclosure.

Hereinafter, exemplary embodiments of the present disclosure will be described in more detail with reference to accompanying drawings.

The present disclosure relates to a dressing for a wound of a human being or an animal. Herein, the dressing body may refer to an article including cloth or fabric to cover at least a portion of the wound. Herein, the article including cloth or fabric may be, for example, a band, a blanket, a cover, a sponge, a bandage, wrap, or the like.

When the skin is wounded, the skin is cured through an infection phase of producing a large amount of exudate, a proliferation phase that granulation formation is actually started, and a maturation phase that neonatal skin is made robust. An embodiment of the present disclosure provides a dressing body for curing a skin, which has an optical curing function to minimize the infection phase by rapidly absorbing exudate in the procedure of curing the wound, to maintain sterilization power to prevent infection by bacteria, and to promote the recovery of the wound.

The present disclosure relates to a dressing body used for a target to be sterilized, that is, a wounded skin of a human being or an animal (hereinafter, referred to as a patient), especially, a dressing body to perform sterilization by applying sterilizing light.

Figure 2:
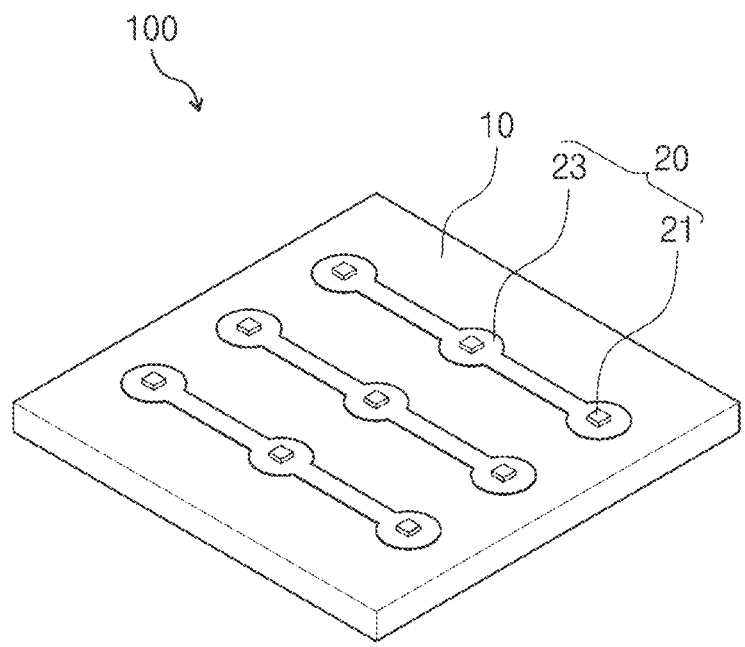
FIG. 2 is a perspective view viewed from the bottom.
Figure 3:
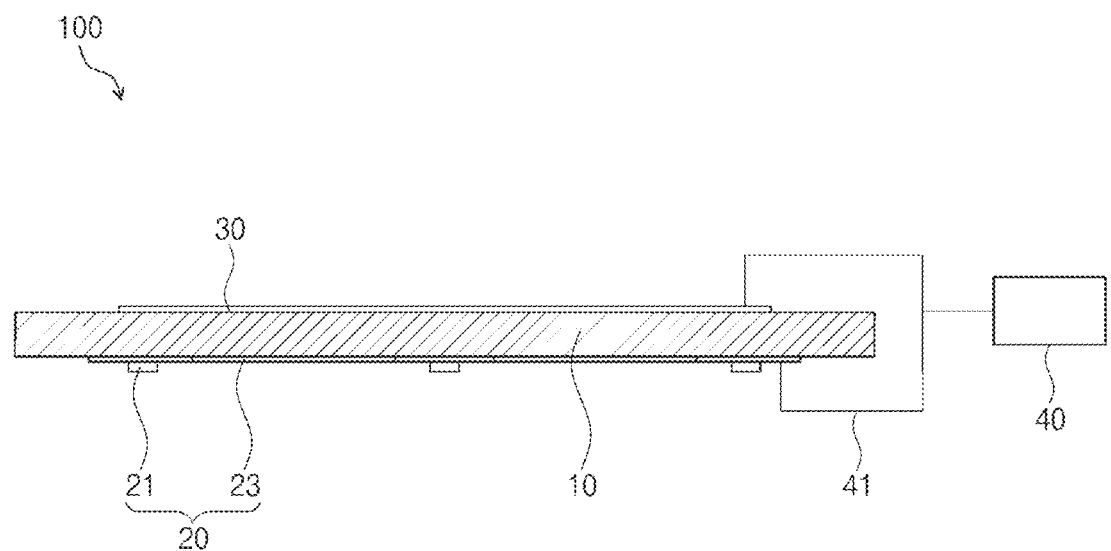
FIG. 3 is a cross-sectional view illustrating a portion of the dressing.

FIG. 1 is an exploded perspective view illustrating according to an embodiment of the present disclosure, and FIG. 2 is a perspective view viewed from the bottom, and FIG. 3 is a cross-sectional view illustrating a portion of the dressing.

Referring to FIGS. 1 to 3, a dressing 100 according to an embodiment of the present disclosure includes a dressing body 10 to cover at least a portion of a wound of a patient to absorb exudate from the wound, a light irradiation device 20 to apply sterilizing light to the wound of the patient, and a display unit 30 to display information on the light irradiation device 20 and the dressing body 10.

According to an embodiment, the term of "exudate" schematically refers to a predetermined exudate (for example, a cell, an infectious byproduct, a cell debris, or a protein) from the wound, which includes predetermined another substance secreted from blood or the wounded part.

The dressing body 10 may be provided in the form to cover at least a portion of the wound of the patient by making direct contact with the wound of the patient. For example, the dressing body 10 may be provided in the shape of a plate having a predetermined thickness, and may be provided in the shape of a circle, an oval, or a rectangle when viewed in a plan view. In addition, the dressing body 10 may have flexibility at a portion or entire portion and have in the flat shape, to effectively cover the wound of the patient. In the present embodiment, when the dressing body 10 has the flat shape, the dressing body 10 has two opposite planes. The two planes are referred to as a first plane and a second plane, respectively. The first plane becomes a surface to make direct contact with the wound while directly facing the wound and the second plane may become a surface exposed to the outside. However, as long as the dressing body 10 has the shape of covering a portion or the entire portion of the wounded part, the dressing body 10 is not limited in thickness or shape, and may be provided in various shapes. According to an embodiment of the present disclosure, for convenience of explanation, it is illustrated by way of example that the dressing body 10 has a predetermined thickness and has the shape of a rectangle when viewed in a plan view.

The dressing body 10 may include a material having porosity to absorb the exudate or having a characteristic of retaining the exudate. For example, the dressing body 10 may be in at least one of a foam dressing type including a polyurethane foam, a hydrocolloid dressing type, a hydrogel dressing type, a porous silicone film dressing type, or a hydrofiber dressing type. The dressing body 10 may be used for a negative pressure wound therapy device.

The dressing body 10 may include a material having flexibility. The dressing body 10 may include a flexible material. Accordingly, it should be considered that the shape of the dressing body 10 is changed to various shapes when external force is applied to the dressing body 10. Although the dressing body 10 is illustrated in the shape of a rectangle in the drawing, the dressing body 10 may have a different shape when applied to the wound of the patient.

According to an embodiment of the present disclosure, the dressing body 10 may contain a medicine to cure the wound of the patient, and the type of the medicine may be variously changed depending on a patient to be applied with the dressing body 10. For example, the medicine may include a therapeutic agent to treat a predetermined symptom, or may include a material, for a pseudo-therapy or non-therapeutic treatment, such as ointment. The medicine may include, for example, for example, a hormone, an antibiotic, an antimicrobial, an antifungal, an anesthetic, an antiseptic, an anti-inflammatory, an antihistamine, an analgesic, an acne medication, an anti-aging compound, a skin moisturizer, a hair growth promoter, a hair growth preventer, a skin growth promoter, a cleanser, or an agent including an arbitrary another beneficial material.

The light irradiation device 20 may sterilize the wound of a patient and a peripheral portion of the wound of a patient by applying sterilizing light to the wound of a patient or the peripheral portion of the wounded part.

The light irradiation device 20 is provided on the first plane of the dressing body 10. The first plane of the dressing body 10, which has the light irradiation device 20, is to face the wounded part. The light irradiation device 20 is provided on the first plane such that the light is applied to the wound of the patient from the light irradiation device 20.

The light irradiation device 20 includes a device board 23 on which a light irradiation device is mounted and at least one light emitting diode 21 is mounted on the device board 23.

The device board 23 may be a printed circuit board printed thereon with a wiring 41 or a circuitry, and may have flexibility or not. According to an embodiment of the present disclosure, when the dressing body 10 is provided to the wound of the patient, the surface of the wound may be a flat surface or not, depending on the position or the shape of the wounded part. When the device board 23 has flexibility or not, even if the surface of the wound is not the flat surface, the device board 23 may be disposed along the surface of the wound. Accordingly, the light irradiation device 20 may effectively apply light to the wound while making closer contact with the surface of the wound.

The device board 23 is mounted facing the wound of the patient. The device board 23 may be provided with a wider area than an area of the light emitting diode 21 such that the light emitting diode 21 is more stably disposed between the dressing body 10 and the wound of the patient, when the dressing body 10 and the light irradiation device 20 are attached to the surface of the wound.

The light emitting diode 21 may emit light in at least one band among ultraviolet light, visible light, and infrared light. A single light emitting diode 21 or a plurality of light emitting diodes 21 may be provided. The light emitting diode 21 may apply the ultraviolet light, the visible light, and the infrared light to the wound of the patient individually, or through the combination thereof depending on the phase of the wound or the curing purpose.

According to an embodiment of the present disclosure, although a total of 9 light emitting diodes 21 are illustrated, the number of the light emitting diodes 21 is not limited thereto. In other words, the number of the light emitting diodes 21 varies depending on the area or the shape of the wound, the phase (for example, an infection phase, a proliferative phase, or a maturation phase) of the wound, or curing purposes.

When a plurality of light emitting diodes 21 are provided, the light emitting diodes 21 may be electrically connected with each other in series, in parallel, or in the combination form of a series type and a parallel type. To this end, although the wiring 41 is not illustrated between the light emitting diodes 21, the wiring 41 may be provided. Although FIG. 1 illustrates the form that the device board 23 extends between mutually adjacent light emitting diodes 21, the present disclosure is not limited thereto. For example, only the wiring 41 may be provided between the mutually adjacent light emitting diodes 21 and the device board 23 may be not provided. Each light emitting diode 21 may receive external power through the wiring 41.

The display unit 30 is provided on the second plane opposite to the first plane on which the light irradiation device 20 is provided.

The display unit 30 may display various pieces of information on the wound of the patient and information necessary to treat the wound of the patient. The information displayed on the display unit 30 may include, for example, information on the patient or information on the dressing 100. Information on the patient may be information on a present phase of the wound of the patient, a time taken for treatment, the pH or the temperature of the wound of the patient, the type or the wavelength of light emitted from the light irradiation device, and time in which the light irradiation device emits light. The information on the dressing 100 includes information on whether power is applied, an alarm of replacement timing of the dressing body 10 depending on whether or not the exudate is absorbed into the dressing body 10, information on whether the light irradiation device 20 operates, or information on whether the light irradiation device 20 or the light emitting diode 21 is replaced.

The display unit 30 may have flexibility or may not have flexibility. The display unit 30 may not have the flexibility since the display unit 30 is attached to the second plane which is an outer surface of the dressing body 10. However, when the display unit 30 has the flexibility, and when the dressing body 10 is deformed along the curve of the wound of the patient, the display unit 30 may be deformed in various manners, such that the dressing body 10 is easily attached to the wound of the patient. For example, when the wound of the patient is present in a narrower area such as a hand or a foot, since the surface of the wound has large curves, it may or may not be easy to attach the display unit 30 to the wound depending on the flexibility of the display unit 30.

The display unit 30, which displays information, may employ various display devices. For example, the various display devices may be an electrophoretic display device, a LED display device, an OLED display device, a liquid crystal display device, or the like.

According to an embodiment of the present disclosure, the dressing 100 may include a controller 40 to control the light irradiation device 20 and the display unit 30. The controller 40 may be connected with the light irradiation device 20 and the display unit 30 through the wiring 41 or through a wireless communication scheme, such as Bluetooth, without the wiring 41.

A mode in which the light emitting diode 21 is powered on is referred to an irradiation mode, and a mode in which the light emitting diode 21 is powered off is an idle mode. The controller 40 may control the irradiation mode and the idle mode of each of the light emitting diodes 21 simultaneously or individually. For example, the controller 40 may control some of the light emitting diodes 21 to be in the irradiation mode, or may control remaining ones of the light emitting diodes 21 to be in the idle mode. In an embodiment of the present disclosure, the controller 40 may control the intensity of light emitted from the light irradiation device 20. The controller 40 may obtain a sterilization effect specific to each target to be sterilized by adjusting the type of a light irradiation device to be irradiated and an amount of irradiation energy for each light irradiation device depending on the target to be sterilized.

For example, contents of photosensitizers vary depending on bacteria. Accordingly, a specific sterilization effect of a specific bacterium may be obtained by adjusting an irradiation amount of predetermined light to each bacterium. Since the UV light induces the damage to DNAs or RNAs existing in substantially all bacteria, the sterilization effect may be produced with respect to all bacteria.

According to an embodiment of the present disclosure, the controller 40 may control an irradiation amount of energy of the light irradiation device 20. The UV light represents an excellent sterilization effect, but the UV light may destroy a cell of a human body according to the same principle. In addition, the UV light may be applied to a normal skin cell to cause the damage to DNA, thereby cause skin cancer. For this reason, the UV light has excellent sterilization power, but the lower safety for a human body, so the UV has a limitation in use for a sterilization purpose. However, in an embodiment of the present disclosure, the controller 40 controls an irradiation amount of light to an extent that UV light is not harmful to the human body when controlling an amount of the UV light. Accordingly, the UV light may be applied to the human body.

According to an embodiment of the present disclosure, the controller 40 may control information displayed on the display unit 30. In addition, the display unit 30 may display various pieces of information on the phase of a wound, a power on/off of the light irradiation device 20, an irradiation amount of light, or irradiation energy, based on information on the patient, by interworking with the controller 40 and the light irradiation device 20.

According to an embodiment of the present disclosure, the light emitting diode 21 is provided in the form of a flip chip having a first electrode and a second electrode. The first electrode and the second electrode of the flip chip may be directly connected with the wiring 41 of the device board 23. The flip chip is significantly smaller than a lateral chip or a vertical chip manufactured in a package form, and is able to be directly mounted on the device board 23.

Figure 4:
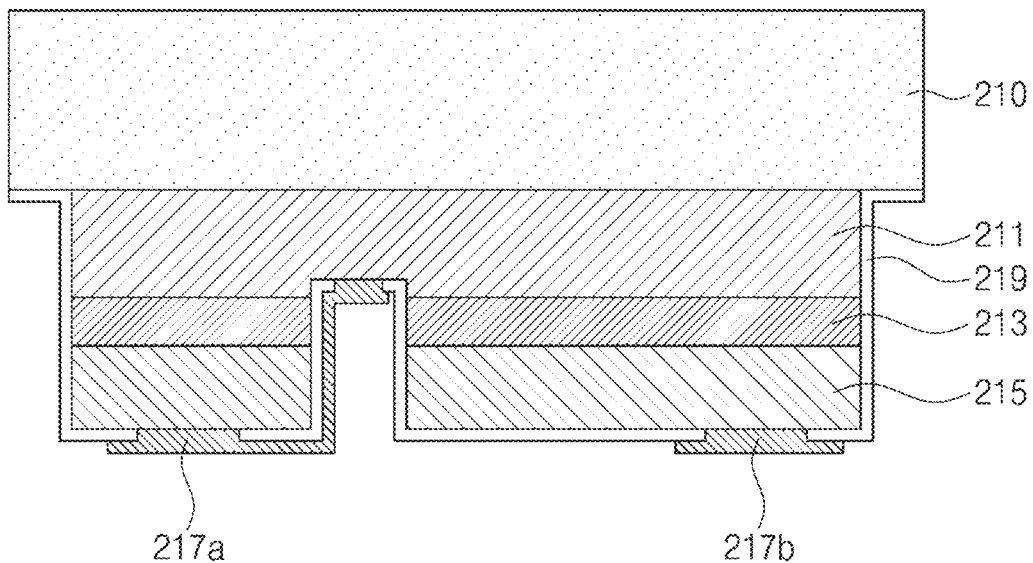
FIG. 4 is a cross-sectional view illustrating a semiconductor chip according to an embodiment of the present disclosure, in which a semiconductor chip in a flip-chip type is illustrated.

FIG. 4 is a cross-sectional view illustrating a semiconductor chip according to an embodiment of the present disclosure, in which a semiconductor chip in a flip-chip type is illustrated.

The flip-chip type of semiconductor may be formed on a substrate, reversed, and mounted on another component. Accordingly, the flip-chip type of semiconductor is illustrated in a reversed form in drawings.

Referring to FIG. 4, the semiconductor chip includes a light emitting stack structure, and first and second electrodes 217a and 217b connected with the light emitting stack structure. The light emitting device stack structure includes a substrate 210 and a first semiconductor layer 211, an active layer 213, a second semiconductor layer 215, a first electrode 217a, a second electrode 217b, and an insulating layer 219 stacked on the substrate 210.

In present embodiment, the light emitting stack structure may include at least one mesa including the active layer 213 and the second semiconductor layer 215. The mesa may include a plurality of protruding patterns, and the plurality of protruding patterns may be spaced from each other. The insulating layer 219 is provided on the mesa. The first electrode 217a is connected to the first semiconductor layer 211 exposed through the contact hole in the mesa, and the second electrode 217b is connected with the second semiconductor layer 215 exposed through a contact hole formed in the second semiconductor layer 215.

As described above, according to an embodiment of the present disclosure, the light emitting diode has the first electrode and the second electrode arranged at the same side. In addition, the light emitting diode is small to be able to easily be mounted on a wiring of the device board. In the present embodiment, the light emitting diode may be provided in micro-size. Accordingly, even if the light emitting diode is provided on one surface of the dressing body, the size of the light emitting diode is significantly small, so the light emitting diode does not affect the whole thickness of the dressing. Therefore, in an embodiment of the present disclosure, the thickness of the dressing may be formed with a thin thickness, so the dressing more closely contacts with the wounded part of the patient.

In particular, even if the light emitting diode is provided on one surface of the dressing body, the protruding extent of the light emitting diode from one surface of the dressing body is very low, so the gap between the wounded part of the patient and the dressing body is rarely formed by the light emitting diode. When the gap between the wounded part of the patient and the dressing body is formed, the efficiency of absorbing the exudate by the dressing body is lowered, and the probability that the dressing body deviates from the wounded part is high. However, in the present disclosure, since the gap between the wounded part of the patient and the dressing body is rarely formed, the above problem does not occur.

The dressing having the above structure may irradiate optical energy to the wound of the patient, thereby sterilizing the wound and inhibiting the infection.

In general, the dressing body prevents secondary infection by blocking the wounded part from the outside, and prevents a scab from being formed on the surface of the wound. However, a conventional dressing body has no function of sterilizing the wound of the patient and function of activating a cell in the wounded part. Accordingly, to promote the recovery of the wound, a separate external medicine has to be applied onto the skin.

To the contrary, in the dressing according to an embodiment of the present disclosure, the light irradiation device is provided on the surface of the dressing body to apply optical energy to the wound, in the state that the patient attaches the dressing body to the wounded part, thereby realizing sterilization and infection inhibition. The dressing according to an embodiment of the present disclosure irradiates light as described above to induce the secretion of substances, which help to cure the wound, from the wounded part and to directly sterilize infectious bacteria, thereby promoting the recovery of the wounded part. Therefore, according to an embodiment of the present disclosure, when the dressing is used, the separate external medicine is not required, and the pathogenic infectious bacteria may be sterilized, and the recovery of the skin cell may be promoted by using optical energy less harmful to a human body.

In detail, for example, according to an embodiment of the present disclosure, the dressing for curing applies blue light or UV light to the wound or the infected part, thereby sterilizing the infectious microorganism and inhibiting infection. In addition, as blue light and/or red light is applied to the wound, the recovery of the skin dermal tissue cells may be promoted. In this case, fibroblasts may be proliferated and collagen production and angiogenesis may be promoted. In addition, blue light and/or red light is applied to a skin epidermal tissue of the wounded part, so the proliferation of keratinocytes is promoted. Accordingly, the recovery of the skin epidermal tissue may be promoted.

In addition, the dressing according to an embodiment of the present disclosure does not cause the problem of the resistance against drugs because a specific drug is not continuously administered.

The dressing according to an embodiment of the present disclosure may be implemented in various forms. Accordingly, hereinafter, various embodiments will be described. The following description will be made while focusing on the difference from above-description, and the part which is not described below can be understood by making reference to the above description.

FIGS. 5 to 9 are a sectional view illustrating the dressing 100, according to an embodiment of the present disclosure.

Figure 5:
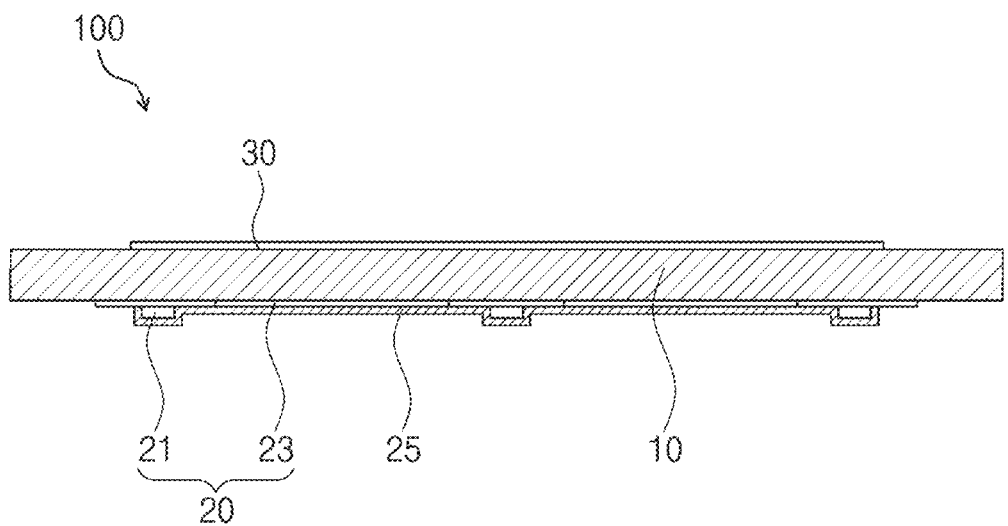
FIG. 5 to FIG. 9 are a sectional view illustrating a dressing, according to an embodiment of the present invention.

Referring to FIG. 5, the dressing 100 may further include a protective film 25 to protect the light emitting diode 21.

According to an embodiment of the present disclosure, the light emitting diode 21 is implemented in the form of a package such that the light emitting diode 21 is protected from external moisture or the exudate in itself, but may be directly mounted on the device board 23 instead of the package form. In this case, the protective film 25 may be provided in the dressing according to an embodiment of the present disclosure to protect the light emitting diode from external moisture or exudate.

The protective film 25 may include a water-proof material to prevent the external moisture or the exudate from being infiltrated into the light emitting diode 21. The protective film 25 may include a water-proof silicone.

In the present embodiment, although it is illustrated that the protective film 25 covers the most part of the device board 23, the present disclosure is not limited thereto. For example, the protective film 25 is provided only for a portion, which corresponds to a region for the light emitting diode 21, of the device board 23. In particular, the protective film 25 may be provided only on the light emitting diode 21 to protect the light emitting diode 21 by surrounding the light emitting diode 21. In this case, since the protective film 25 includes a water-proof material, if a wider protective film is provided, water or exudate discharged from the wound the patient may be prevented from being absorbed into the dressing body 10. Accordingly, the protective film 25 may be formed with the minimum area sufficient to protect the light emitting diode 21.

Figure 6:
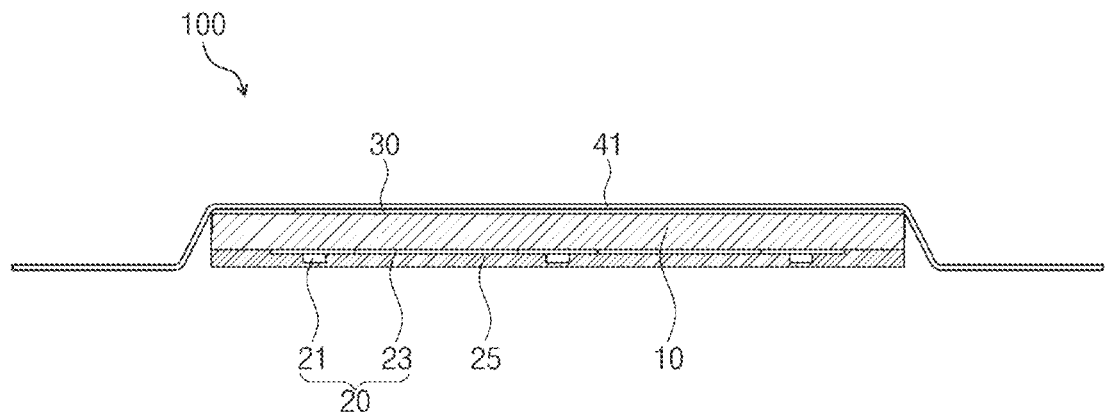

Referring to FIG. 6, an adhesive member 41 may be provided on the dressing such that the dressing is easily attached to the wound of the patient, according to an embodiment of the present disclosure.

The adhesive member 41 is used to attach or fix the dressing body 10 to the wound of the patient. The adhesive member 41 may cover the dressing body 10 or may be provided around the dressing body 10. For example, as illustrated in FIG. 6, the adhesive member 41 may be provided in the form of directly contacting with a skin by extending the peripheral portion of the dressing body 10 while covering the entire portion of the dressing body 10. However, the form of the adhesive member 41 is not limited thereto, but may cover only a portion of the dressing body 10 and may have the form of a tape.

According to an embodiment of the present disclosure, the adhesive member 41 may be provided in the form of a film having flexibility to easily adhere to the wound of the patient. For example, the adhesive member 41 may be provided with a thickness thinner than the thickness of the dressing body 10. In this case, although the adhesive member 41 is separately illustrated, the adhesive member 41 may be provided in the form obtained by applying an adhesive onto a polymer film.

In an embodiment of the present disclosure, the protective film 25 may be formed differently from the form described above, regardless of the adhesive member 41. In the present embodiment, the protective film 25 may be provided with the thickness sufficient to cover the step difference between the light emitting diode 21 and the device board 23. This is necessary to minimize that a skin at a position where corresponds to the light emitting diode 21 being provided is squashed when the dressing body 10 is attached as the light emitting diode 21 is mounted on the device board 23 while protruding, and to reduce stress applied to the light emitting diode 21.

In addition, a diffusion layer may be further provided on the protective film 25 to diffuse light emitted from the light emitting diode 21. The diffusion layer may be provided in the form of a separate layer, on the protective layer 25, or may be formed integrally with the protective film 25. In addition, the diffusion layer may include a diffusion pattern to diffuse light. According to an embodiment of the present disclosure, the diffusion pattern may be provided in the form that the surface of the diffusion pattern has roughness.

Figure 7:
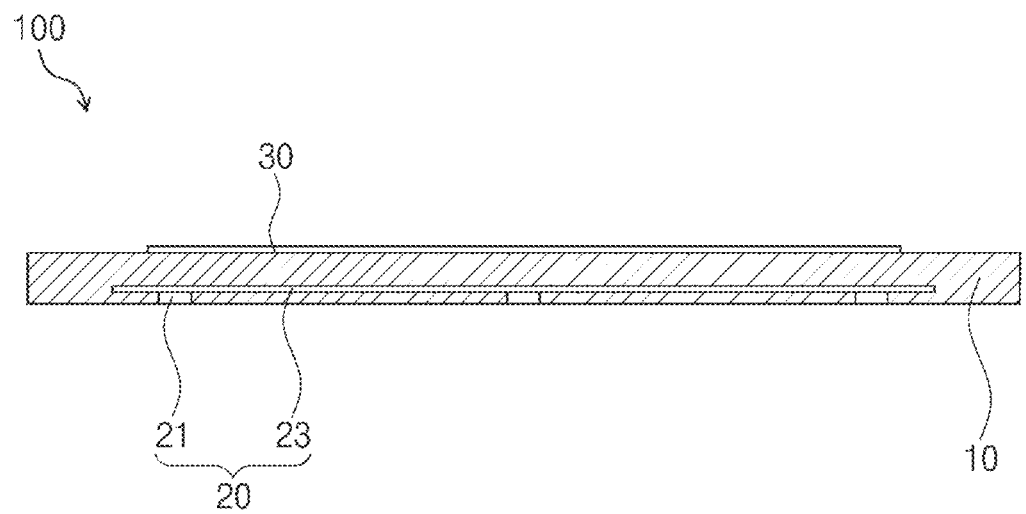

Referring to FIG. 7, in the dressing according to an embodiment of the present disclosure, the light irradiation device 20 may be provided in the inner part of the dressing body 10, instead of being provided on the first plane of the dressing body 10. In this case, even if the light irradiation device 20 is provided in the inner part of the dressing body 10, the light irradiation device 20 is provided at a position in which light from the light emitting diode 21 of the light irradiation device 20 arrives at the wound of the patient. For example, when the dressing body 10 is formed of a light transmitting material, the light irradiation device 20 may be disposed every place inside the dressing body 10. However, when the dressing body 10 is not formed of the light transmitting material, the light irradiation device 20 has to be disposed at a point closes to the first plane of the dressing body 10, such that light arrives at the wound through the first plane of the dressing body 10. Alternatively, a potion, which corresponds to a part for the light emitting diode 21 of the light irradiation device 20, of the dressing body 10 may be removed, and the light may arrive at the wound through the removed portion.

Figure 8:
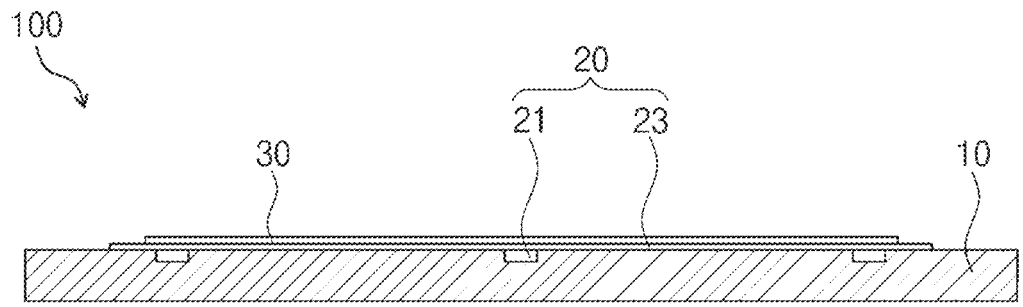

Referring to FIG. 8, in the dressing according to an embodiment of the present disclosure, the light irradiation device 20 may be interposed between the display unit 30 and the dressing body 10. In this case, the dressing body 10 may be formed of a light transmitting material such that light arrives at the wound of the patient from the light emitting diode 21 of the light irradiation device 20.

When the light irradiation device 20 is interposed between the display unit 30 and the dressing body 10, since the light from the light emitting diode 21 is provided throughout the entire portion of the dressing body 10, the dressing body 10 may be sterilized. The dressing body 10 is absorbed with the exudate discharged from the wound of the patient. Accordingly, bacteria may easily propagate. Accordingly, the dressing body 10 is sterilized by the light from the light emitting diode 21, thereby preventing the wound of the patient from experiencing secondary infection.

In an embodiment of the present disclosure, when the light irradiation device 20 is interposed between the display unit 30 and the dressing body 10, the display unit 30 may be formed integrally with the display unit 30. In other words, the light irradiation device 20 and the display unit 30 are manufactured in the form of one electronic device, which is to be mounted on the second plane of the dressing body 10.

Figure 9:
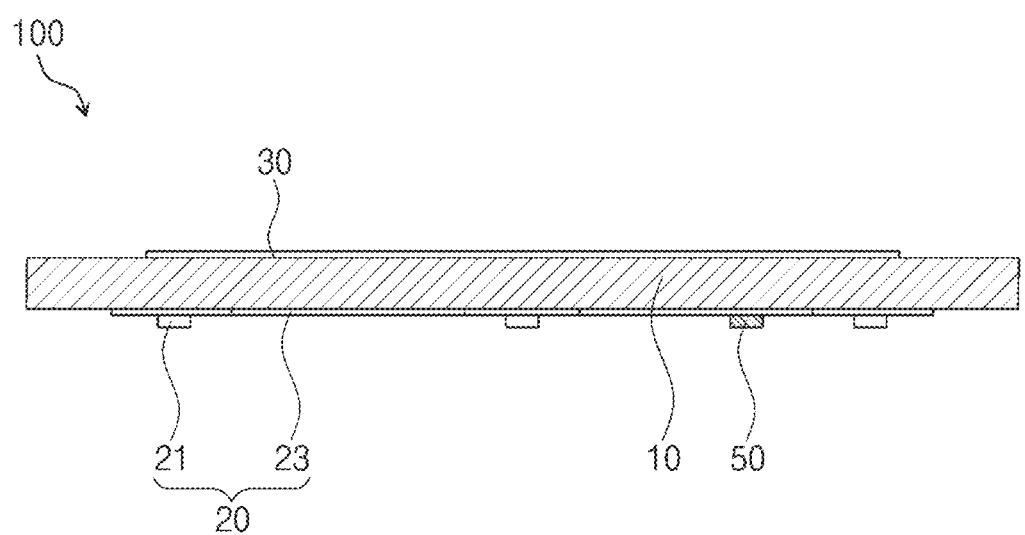

Referring to FIG. 9, the dressing according to an embodiment of the present disclosure may include a sensor unit 50 to sense the state of the wound of the patient, the state of the light irradiation device 20, or the state of the dressing, especially, the state of the dressing body 10.

The sensor unit 50 may include a single sensor unit, or a plurality of sensor units, and may be inside or outside the dressing body 10. For example, the sensor unit 50 may be provided on the first plane of the dressing body 10 and/or the second plane of the dressing body 10.

When the sensor unit 50 is to sense the state of the patient, the sensor unit 50 may be a temperature sensor or pH sensor. For example, as the temperature of the wound part of the patient is increased in the process that the wound part of the patient is cured, the sensor unit may sense the temperature of the wound part of the patient to detect the phase of the wound part. In addition, when the exudate is discharged from the wound of the patient, pH may be varied depending on the exudate. Accordingly, the sensor unit may sense the discharge of the exudate to obtain the information on the wound of the patient. However, the type of the sensor unit 50 is not limited thereto. For example, various types of sensors may be used as long as the sensors can detect the state of a patient.

When the sensor unit 50 is to sense the state of the light irradiation device 20, the sensor unit 50 may be an optical sensor. The sensor unit may sense an amount of light, the intensity of the light, and wavelength information from the light irradiation device 20. Accordingly, the sensor unit 50 may sense the replacement timing of the light irradiation device 20 or may sense whether the light irradiation device 20 operates exactly.

In particular, the dressing body 10 is substantially a disposable dressing body, and needs to be replaced with a new dressing body 10 in various cases such as the case that the dressing body 10 is expanded by absorbing the exudate. In an embodiment of the present disclosure, when the dressing body 10 needs to be replaced with a new one as the dressing body 10 is expanded by absorbing the exudate, contaminated with another substance, or damaged, only the dressing body 10 may be separated from the display unit 30 and the light irradiation device 20, replaced with a new dressing body 10, and mounted on the display unit 30 and the light irradiation device 20.

Figure 10A:
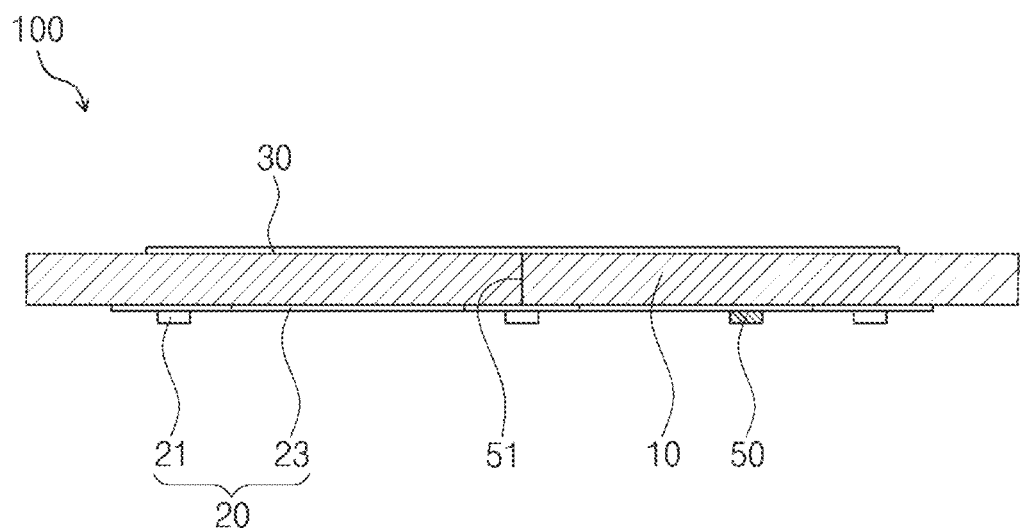
FIGS. 10A and 10B are cross-sectional views illustrating that a sensor unit includes additional components to sense the state of a dressing body.
Figure 10B:
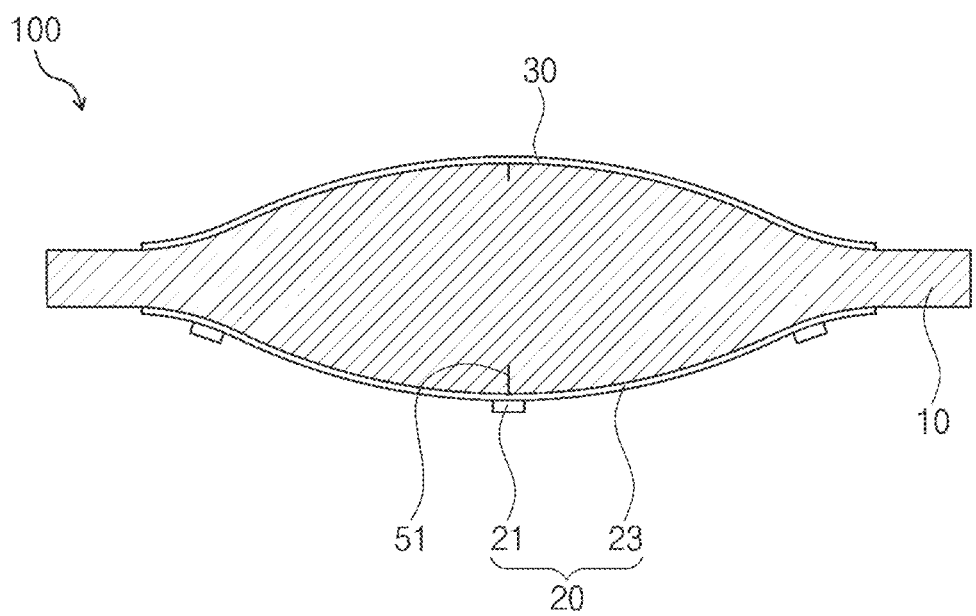

FIGS. 10A and 10B are cross-sectional views illustrating that the sensor unit includes additional components to sense the state of the dressing body.

Referring to FIGS. 10A and 10B, the sensor unit 50 may further include a sensing wiring 51 to determine whether the dressing body 10 is expanded. The sensing wiring 51 is to to sense whether the dressing body 10 is expanded, the display unit 30 may show a need to replace the dressing body 10 when the expansion of the dressing body 10 is identified.

The sensing wiring 51 may include a conductive wire 41 to connect the first plane with the second plane of the dressing body 10. The sensing wiring 51 may be provided such that the sensing wiring 51 is easily broken by external force. When the dressing body 10 is expanded by absorbing the exudate, the distance between the first plane and the second plane is increased, force is vertically applied to the sensing wiring 51 to connect the first plane with the second plane. The sensing wiring 51 may be broken by the applied force. The sensor unit 50 may sense the sensing wiring 51 broken, thereby easily determining whether the dressing body 10 is expanded.

In the present embodiment, although the sensing wiring has been described in that the sensing wiring determines whether the dressing body is expanded, this is merely provided for the illustrative purpose. For example, it is obvious that another type of a sensor unit may be provided to determine the expansion sate or the replacement state of the dressing body. For example, a magnetic force sensor may be used as a sensor to determine whether the dressing body is expanded.

As described above, the dressing body may be mainly provided as a disposable dressing body. When the dressing body 10 is expanded by absorbing the exudate, the dressing body 10 needs to be replaced with a new dressing body. In this case, the exudate may be steadily efficiently absorbed by replacing only the dressing body in the state that another component of the dressing is maintained.

FIG. 11 is a cross-sectional view illustrating the dressing according to an embodiment of the present disclosure, in which the dressing body is mounted on the light irradiation device and the display unit.

Referring to FIG. 11, in the dressing according to an embodiment of the present disclosure, the dressing body 10 may be detachably provided. Accordingly, the dressing body 10 having the exudate absorbed therein is removed from the light irradiation device 20 and the display unit 30, and a new dressing body 10 may be mounted on the light irradiation device 20 and the display unit 30. In this case, different components such as the light irradiation device 20, the display unit 30, and the controller 40 may be maintained without being replaced.

In present embodiment, the disposable dressing body is replaced, and the display unit or the light irradiation device, which is available for a long time, is utilized again. Accordingly, when the dressing is used, the sanitary state may be maintained while the discharge of waste is minimized and the cost of consumables is minimized.

As described above, the display unit, the light irradiation device, and the sensor unit may be provided in the dressing according to an embodiment of the present disclosure, and the display unit, the light irradiation device, and the sensor unit may be connected with the controller to interwork with each other. For example, the display unit and the sensor unit may interwork with each other, and the display unit may output data sensed by the sensor unit. Alternatively, as the light irradiation device interworks with the sensor unit, the wavelength and the output intensity of the light emitted from the light emitting diode may be set.

In an embodiment of the present disclosure, an oxygenator may be selectively provided to the light irradiation device 20. The oxygenator is connected with the controller 40 such that the oxygenator is turned on/off. When the oxygenator is turned on, oxygen is supplied to a target. A manner of supplying oxygen is not specified, and may include a manner of increasing the contact count with air by stirring a liquid using a stirrer, as well as a manner of providing oxygen to the target through a nozzle. For example, when light is irradiated to a specific fluid, at least one of the first and the second light may be irradiated to the fluid while stirring the fluid using the stirrer. Alternatively, when light is irradiated to a place such as a skin of a human being, oxygen is supplied to the skin through a separate nozzle, which spurts oxygen, while at least one of the first light and the second light is being irradiated to the skin.

In an embodiment of the present disclosure, since the sterilization power may be remarkably increased when the oxygen is provided in irradiating light as described above, the oxygen is smoothly provided into a cell in the case of, especially, 405-nm light. Accordingly, the production of the reactive oxygen species is promoted in the cell of the bacteria, thereby accelerating the destruction of the bacteria Although not illustrated, an input unit may be further provided in the dressing according to an embodiment of the present disclosure such that a doctor, a nurse, or a patient inputs information on the patient. The information on the patient may include various types of information including the diagnostic result of the doctor, the nurse, or the patient or the result of an image captured by the camera. In this case, the input unit may be provided in the form of an electronic module integrated with the controller.

The controller may control the light irradiation device and the display unit, based on the information on the patient obtained from the doctor, the nurse, or the patient, and information obtained from the sensor unit. In this case, a preset recipe may be provided with respect to a manner of driving the light irradiation device and the display unit depending on the state of the wound and the phase of the wound The recipe may include a light amount, an intensity of light, a wavelength type of light, or an irradiation time of the light which is appropriate to the state of the wound, and the display unit may selectively display the information on the display unit. In this case, a user, such as the doctor, the nurse, or the patient, who uses the dressing, may personally select or set the driving state or the driving manner of the light irradiation device and the display unit through the controller, based on the information of the patient. The driving state of the light irradiation device and the display unit may be automatically set as well as the direct setting by the user.

For example, when the phase of the wound is an infection phase, UV light or light in blue wavelength band advantageous to the sterilization and the infection inhibition may be set to be irradiated to the wound part. When the phase of the wound part is a proliferation phase, light in green or blue wavelength band, which is effective to proliferate fibroblasts, to produce collagen, and to promote angiogenesis, is set to be applied to the wound part. When the phase of the wound is the maturation phase, the light in the red light wavelength or the UV wavelength band, which is effective to circulate blood, or proliferate keratinocyte, may be set to be irradiated to the wound part.

As described above, the controller may automatically or manually control the light emitting diode of the light irradiation device to emit light or not to emit light, depending on the wound phase of the patient.

Although an exemplary embodiment of the present disclosure has been described for illustrative purposes, those skilled in the art will appreciate that various modifications, and substitutions are possible, without departing from the scope and spirit of the present disclosure as disclosed in the accompanying claims.

According to an embodiment of the present disclosure, various modifications are possible without departing from the above-described concept. Hereinafter, another embodiment of the present disclosure will be described with reference to accompanying drawings.

The following description will be made while focusing on the difference to avoid redundancy, and reference to the above-description will be made for the purpose of understanding of parts which are not described below.

Figure 12:
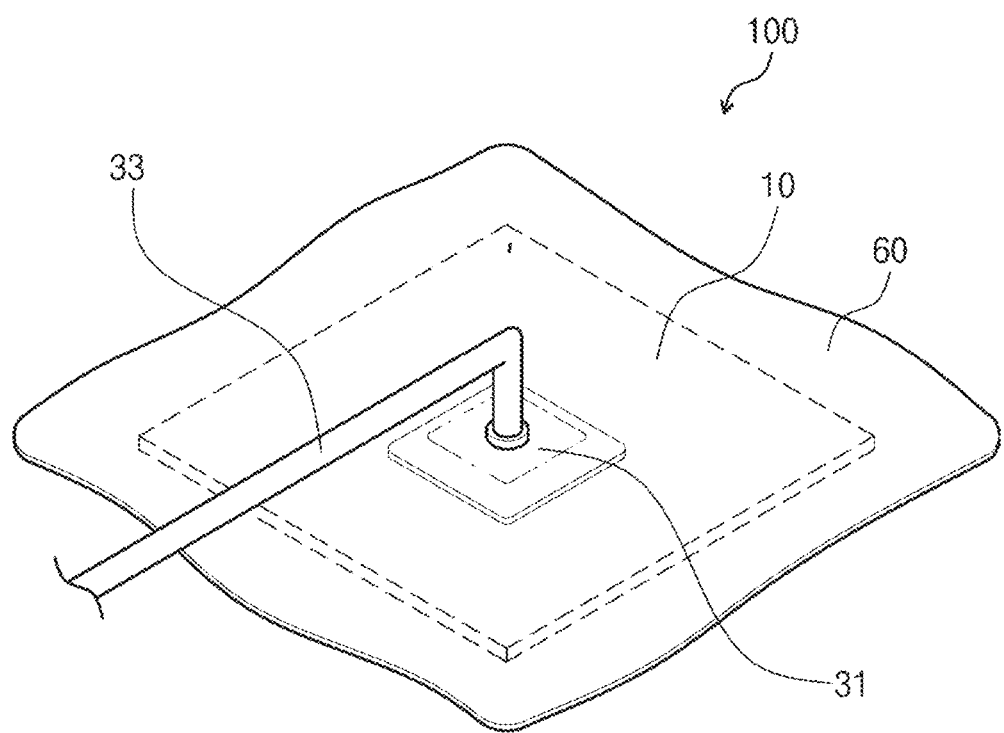
FIG. 12 is a perspective view illustrating a dressing according to an embodiment of the present disclosure.
Figure 13:
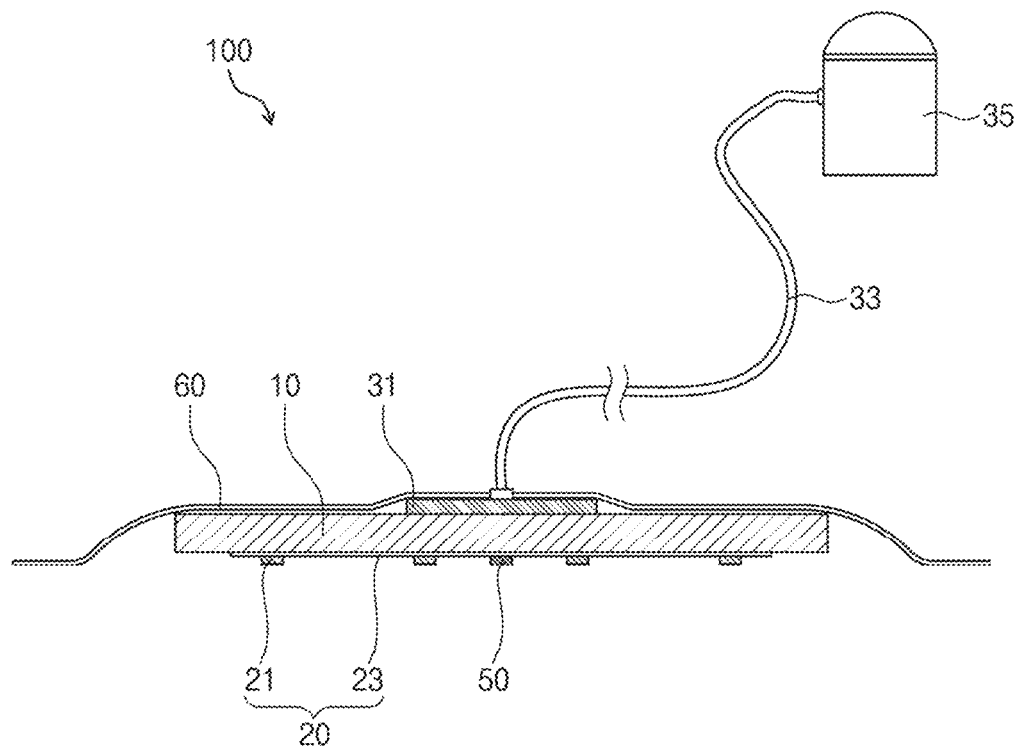
FIG. 13 is a cross-sectional view of a dressing of FIG. 12.
Figure 14:
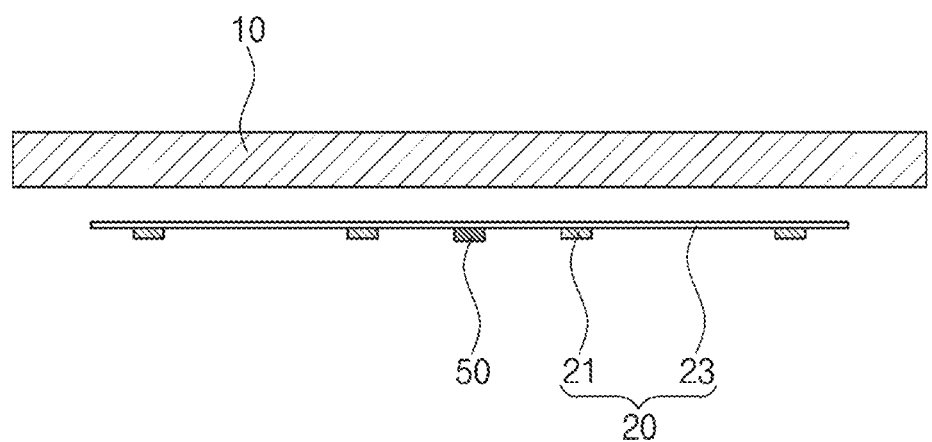
FIG. 14 is a cross-sectional view separately illustrating a dressing body and a light irradiation device according to an embodiment of the present disclosure.
Figure 15:
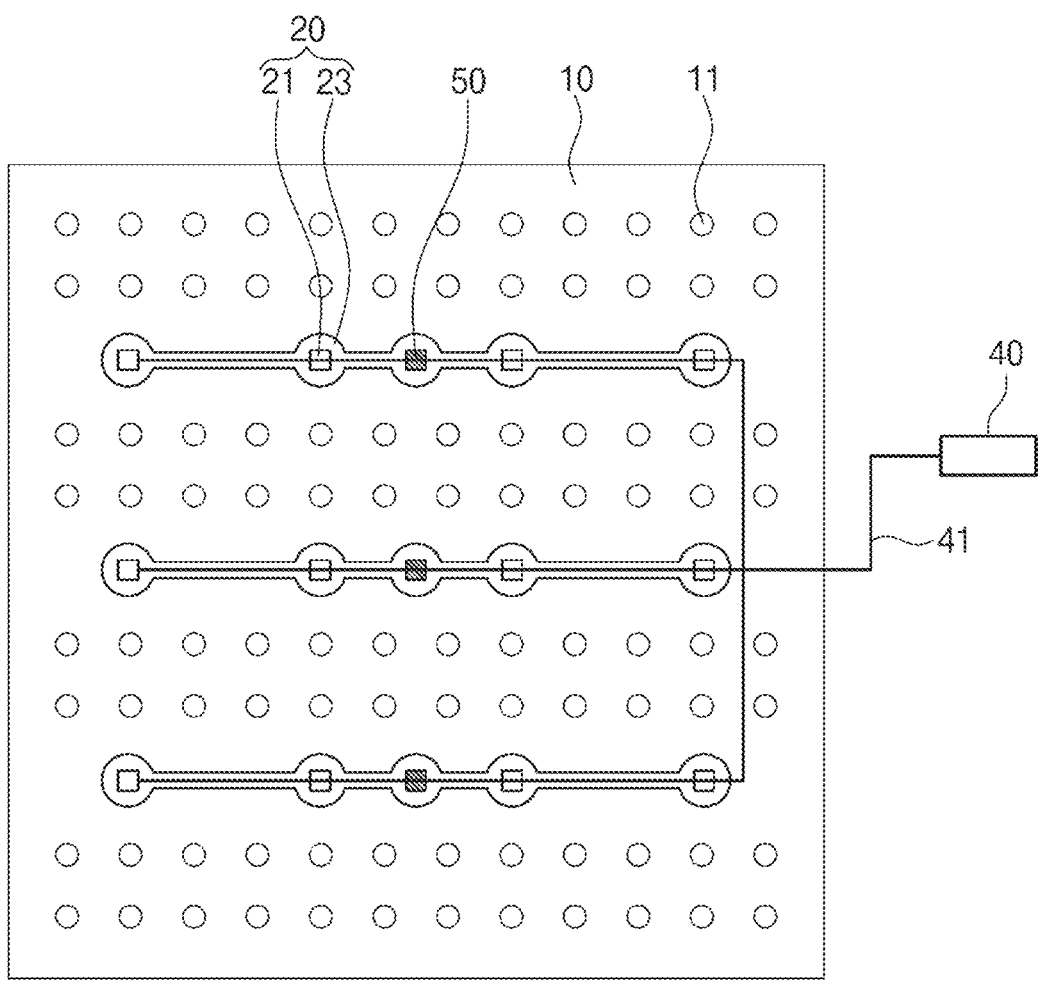
FIG. 15 is a plan view illustrating a dressing body and a light irradiation device when viewed from the bottom.

FIG. 12 is a perspective view illustrating a dressing for negative pressure wound therapy according to an embodiment of the present disclosure, and FIG. 13 is a cross-sectional view of the dressing for negative pressure wound therapy of FIG. 12. FIG. 14 is a sectional view separately illustrating a dressing body and the light irradiation device according to an embodiment of the present disclosure, and FIG. 15 is a plan view illustrating the dressing body and the light irradiation device when viewed from the bottom.

Although FIG. 14 illustrates the dressing body spaced apart from the light irradiation device for the illustrative purpose, the light radiation is actually provided in contact with a first surface (that is, a bottom surface when viewed in drawings) of the dressing body.

Referring to FIGS. 12 to 15, a dressing 100 according to an embodiment includes a drape 60 to form an inner space, which is in contact with a wounded part, by covering the wounded part, a dressing body 10 provided in the inner space, a negative pressure generating member to communicate with the inner space to apply the negative pressure to the inner space, a tube 33 to connect the inner space with the negative pressure generating member, and a light irradiation device 20 provided in the inner space to apply light to the wounded part.

According to an embodiment, the term of "exudate" schematically refers to a predetermined exudate (for example, a cell, an infectious byproduct, a cell debris, or a protein) from the wound, which includes predetermined another substance secreted from blood or the wounded part.

The drape 60 is provided in an area to cover the entire portion of the wounded part when viewed in a plan view, and forms the inner space in a region for the wounded part by adhering to a skin close to the wounded part, for example, a skin surrounding the wounded part. The inner space is a region surrounded by the drape 60 and the wounded part and the exudate secreted from the wounded part is discharged into the inner space.

The drape 60 has flexibility and stably adheres to the wounded part as an adhesive member is provided to at least a partial region of the drape 60. According to an embodiment of the present disclosure, the adhesive member may be provided in the form of a film having flexibility to easily adhere to the wounded part. For example, the adhesive member 41 may be provided with a thickness thinner than the thickness of the dressing body 10. In this case, although the adhesive member is separately illustrated, the adhesive member may be provided in the form obtained by applying an adhesive onto a polymer film.

The dressing body 10 is provided in the inner space defined by the drape 60 and the wounded part to absorb the exudate. The dressing body 10 may include a porous material to easily absorb the exudate from the wounded part and then to easily discharge the exudate from the outside through the tube 33. When the dressing body 10 includes the porous material, the dressing body 10 may have an exudate opening 11 to absorb the exudate from the wounded part. Although the drawing illustrates that the exudate opening 11 is provided in the form of a hole having a predetermined diameter, the diameter of the exudate opening 11 is not limited thereto. In other words, the exudate opening 11 may be formed in smaller size or larger size as long as the exudate opening 11 absorbs or discharge exudate. In addition, the drawing illustrates that exudate openings 11 are regularly arranged, but are not limited thereto. For example, the exudate openings 11 may be randomly arranged.

The dressing body 10 may make direct contact with the wounded part.

The dressing body 10 may be provided in the form to cover at least a portion of the wounded part. The dressing body 10 may include a material having porosity to absorb the exudate or having a characteristic of retaining the exudate. The dressing body 10 may include a material having flexibility. The dressing body 10 may include a material having flexibility. Accordingly, it should be considered that the shape of the dressing body 10 is changed to various shapes when external force is applied to the dressing body 10. Although the dressing body 10 is illustrated in the shape of a rectangle in the drawing, the dressing body 10 may have a different shape when applied to the wounded part.

According to an embodiment of the present disclosure, the dressing body 10 may contain a medicine to heal the wounded part, and the type of the medicine may be variously changed depending on a patient to be applied with the dressing body 10.

According to an embodiment of the present disclosure, the dressing body 10 may include a flexible porous material, may be deformed in an outer shape thereof at a negative pressure atmosphere, when the inner space is at the negative pressure atmosphere formed by a negative pressure generating member to be described, and may provide the absorbed exudate to the tube 33.

The negative pressure generating member is connected with the inner space defined by the drape 60 and the wounded part. In other words, the negative pressure generating member communicates with the inner space.

The negative pressure generating member includes a negative pressure generating module 35 equipped with a negative pressure pump, a tube 33 to connect the negative pressure generating module 35 with the inner space, and a tube connector 31 provided at a part of the drape 60, which is positioned at the side of the wounded part, to connect the tube 33 with the inner space such that the tube 33 communicates with the inner space. The tube connector 31 may be provided with rigidity, which is different from a flexible component such as the drape 60 or the dressing body 10.

The negative pressure pump in the negative pressure generating module 35 is an appliance to form the negative pressure atmosphere in the inner space. The negative pressure atmosphere formed by the negative pressure pump is atmospheric pressure lower than the atmospheric pressure (760 mmHg). The negative pressure atmosphere formed by the negative pressure pump is provided into the inner space through the tube 33.

The tube 33 is a passage allowing the exudate, which is introduced through the dressing body 10, of the wounded part to flow, when the negative pressure atmosphere is provided into the inner space as the negative pressure pump operates. The tube 33 may be detachably connected with the drape 60 or the tube connector 31.

Although not illustrated, a suction vessel may be additionally provided at one end portion of the tube 33 such that the discharged exudate is collected. Accordingly, the exudate may be discharged to the external suction vessel through the tube 33 at the negative pressure atmosphere and disposed.

The light irradiation device 20 may sterilize the wounded part and/or a peripheral portion thereof, by applying sterilizing light to the wounded part and/or the peripheral portion of the wounded part.

The light irradiation device 20 is provided on the first plane of the dressing body 10. The first plane, which is provided thereon with the light irradiation device 20, of the dressing body 10 is to face the wounded part. The light irradiation device 20 is provided on the first plane such that the light is applied to the wounded part from the light irradiation device 20.

The light irradiation device 20 includes a device board 23 on which a light source is mounted and at least one light emitting diode 21 mounted on the device board 23.

In dressing according to an embodiment of the present disclosure, a sensor unit may be provided in the inner space to sense various pieces of information in the inner space. The sensor unit may sense various pieces of information using various sensors. For example, the sensor unit may include sensors that detect the state of the wounded part, the state of the light irradiation device 20, the state of the dressing for negative pressure. Particularly, the sensor unit may include sensors to sense the state of the dressing body 10. More particularly, the sensor unit may include a pressure sensor 50 to sense the state of the negative pressure atmosphere. Various types of pressure sensors 50 may be provided as long as the pressure sensors 50 sense internal pressure.

A single sensor, or a plurality of sensors may be provided, and may be inside or outside the dressing body 10. For example, a plurality of pressure sensors 50 may be provided on the light irradiation device 20 disposed on the first plane of the dressing body 10. Accordingly, in detail, a plurality of pressure sensors 50 (three pressure sensors in drawings may be provided on the device board 23 of the light irradiation device 20.

When the sensor unit includes a sensor to sense the state of the wounded part, the sensor may include a temperature sensor or a pH sensor. For example, as the temperature of the wounded part is increased in the process that the wounded part is cured, the sensor unit may sense the temperature of the wounded part to detect the phase of the wounded part. In addition, when the exudate is discharged from the wounded part, pH may be varied depending on the exudate. Accordingly, the sensor unit may sense the discharge of the exudate to obtain the information on the wounded part. However, the type of the sensor is not limited thereto. For example, various types of sensors may be used as long as the sensors detect the state of a patient.

When the sensor unit is to sense the state of a light irradiation device 20', the sensor unit may be an optical sensor. The sensor unit may sense an amount of light, the intensity of the light, and wavelength information from the light irradiation device 20. Accordingly, the sensor unit may sense the replacement timing of the light irradiation device 20 or may sense whether the light irradiation device 20 operates exactly.

According to an embodiment of the present disclosure, the dressing 100 for negative pressure wound therapy may include a controller 40 to control the light irradiation device 20 and the sensor unit. The controller 40 may be connected with the light irradiation device 20 and the sensor unit through the wiring 41 or through a wireless communication scheme, such as Bluetooth, without the wiring 41.

In an embodiment of the present disclosure, the controller 40 may control the light irradiation device 20 based on information sensed by the sensor unit. For example, the controller 40 may turn on the power of the light irradiation device 20 only when the pressure sensor 50 of the sensor unit senses that the negative pressure is applied into the inner space, and may turn off the power of the light irradiation device 20 when the pressure sensor 50 fails to sense that negative pressure is applied into the inner surface. In addition, a user may variously change the phase of a wounded part, a power on/off of the light irradiation device, an irradiation amount of light, or irradiation energy, based on information of the patient, by interworking with the controller 40 and the light irradiation device 20.

Although not illustrated in drawings, the light irradiation device 20 of the dressing 100 for negative pressure may further include a protective film formed on the light emitting diode 21 to protect the light emitting diode 21. According to an embodiment of the present disclosure, the light emitting diode 21 is implemented in the form of a package such that the light emitting diode 21 is protected from external moisture or the exudate in itself, but may be directly mounted on the device board 23 instead of the package form. In this case, a protective film may be provided in the dressing 100 for negative pressure according to an embodiment of the present disclosure to protect the light emitting diode 21 from external moisture or exudate. The protective film may include a water-proof material to prevent the external moisture or the exudate from being infiltrated into the light emitting diode 21. The protective film may include a water-proof silicone.

In the present embodiment, the protective film may cover most parts of the device board 23, or may be provided only for a portion, which corresponds to a region for the light emitting diode 21, of the device board 23. In particular, the protective film may be provided only on the light emitting diode 21 to protect the light emitting diode 21 by surrounding the light emitting diode 21. In this case, since the protective film includes a water-proof material, if a wider protective film is provided, water or exudate discharged from the wounded part may be prevented from being absorbed into the dressing body 10. Accordingly, the protective film may be formed with the minimum area sufficient to protect the light emitting diode 21.

According to an embodiment of the present disclosure, the light emitting diode 21 is provided in the form of a flip chip having a first electrode and a second electrode. The first electrode and the second electrode of the flip chip may be directly connected with the wiring 41 of the device board 23. The flip chip is significantly smaller than a lateral chip or a vertical chip manufactured in a package form, and is able to be directly mounted on the printed circuit board 23.

The dressing 100 for negative pressure, which has the above-described structure, may sterilize pathogenic infectious bacteria using sterilizing light and may recover a skin cell.

In particular, a dressing for negative pressure wound therapy suctions according to a prior art suctions exudate from a peripheral portion of a wound and recovers the wound, by using a negative pressure device coupled to the dressing, in the state that a patient wears a device for 24 hours. However, the dressing according to the prior art has no function of sterilizing an inner part of the wound, so the treatment by a separate external medicine is required. In addition, when the negative pressure device is simply used, only exudate is discharged and any sterilization and wound recovering effect is not expected.

To the contrary, in the dressing for negative pressure wound therapy according to an embodiment of the present disclosure, the light irradiation device is provided on the surface of the dressing body to apply optical energy to the wounded part, in the state that the patient attaches the dressing body to the wounded part, thereby realizing sterilization and infection inhibition effects. The dressing for negative pressure wound therapy according to an embodiment of the present disclosure irradiates light as described above to induce the secretion of substances, which help cure the wounded part, from the wounded part and to directly sterilize infectious bacteria, thereby promoting the recovery of the wounded part. Therefore, according to an embodiment of the present disclosure, when the dressing for negative pressure wound therapy is used, the separate external medicine is not required, and the pathogenic infectious bacteria may be sterilized, and the recovery of the skin cell may be promoted by using optical energy less harmful to a human body.

Further, the sensor unit such as a separate pressure sensor is provided for the dressing. Accordingly, when the negative pressure pump operates, so the negative pressure is exactly applied to the wound part, the light irradiation device may be set to be turned on. Accordingly, the risk that a skin is exposed to specific light except for the wounded part is significantly reduced.

In addition, the dressing for negative pressure wound therapy according to an embodiment of the present disclosure does not cause the problem of the resistance against drugs because a specific drug is not continuously administered.

The dressing for negative pressure wound therapy according to an embodiment of the present disclosure may be implemented in various forms. Accordingly, hereinafter, various embodiments will be described. The following description will be made while focusing on the difference from above-description, and the part which is not described below can be understood by making reference to the above description.

Figure 16A:
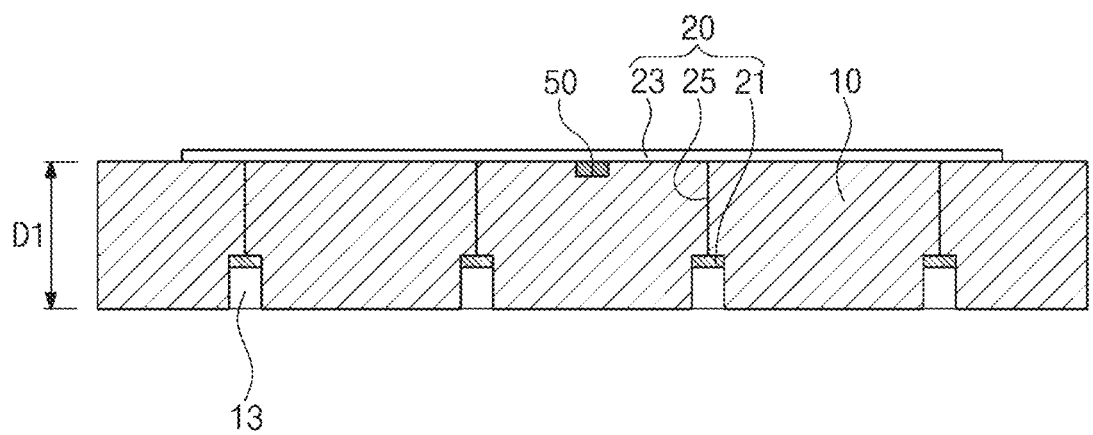
FIGS. 16A and 16B are cross-sectional views illustrating a dressing body and a light irradiation device in a dressing according to an embodiment of the present disclosure.
Figure 16B:
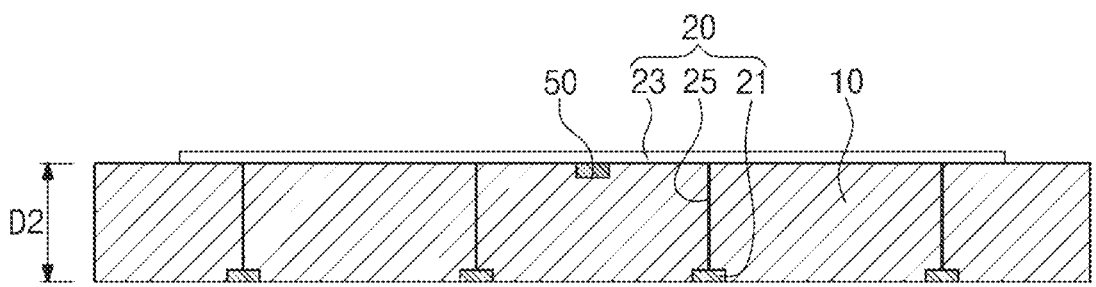

FIGS. 16A and 16B are cross-sectional views illustrating the dressing body 10 and the light irradiation device 20 in the dressing for negative pressure wound therapy according to an embodiment of the present disclosure.

In the present embodiment, the light emitting diode 21 may be provided in the form of being spaced apart from the device board 23 through a separate power wiring 25 without being directly mounted on the device board 23. In this case, the light emitting diode 21 may be provided inside the dressing body 10.

According to an embodiment of the present disclosure, the light emitting diode 21 is provided inside the dressing body 10, so the dressing body 10 may be sterilized by light emitted from the light emitting diode 21. The dressing body 10 has the exudate absorbed from the wounded part and the exudate has infectious bacteria removed from the wounded part. Accordingly, the wounded part may have secondary infection by the exudate absorbed into the dressing body 10. However, when the light emitting diode 21 is provided inside the dressing body 10, the light emitted from the light emitting diode 21 may sterilize the dressing body 10 to prevent or minimize the secondary infection.

When the dressing for negative pressure wound therapy is applied to the wounded part and the negative pressure is applied to the wounded part, the dressing body 10 may be contracted due to the negative pressure and the light emitting diode 21 may be exposed toward the wounded part through such contraction. For example, when the negative pressure is not applied to the dressing body 10, and the dressing body 10 has the first thickness D1, the light emitting diode 21 is disposed at a distance smaller than the first thickness D1 from the device board 23 provided on the second plane of the dressing body 10. The power wiring 25 to connect the light emitting diode 21 with the device board 23 may be provided on a separate substrate or may include a hard material. In addition, the power wiring 25 may be provided with the equal length without contraction, expansion, or bending even if the negative pressure is applied. In the present embodiment, the distance, at which the light emitting diode 21 is disposed, corresponds to a position corresponding to a thickness of the dressing body 10 when the negative pressure is applied. If the dressing body 10 has a second thickness D2 when the negative pressure is applied to the dressing, the distance from the light emitting diode 21 to the device board 23 is substantially equal to the second thickness D2.

Accordingly, as the dressing body 10 is contracted when the negative pressure is applied to the inner space, the light emitting diode 21 may be exposed to the outside from the first plane of the dressing body 10, so the light is efficiently applied to the wounded part.

In this case, a light emission opening 13 is provided in a region, in which the light emitting diode 21 is provided, to prevent the interruption in the contraction of the dressing body 10, when the dressing body 10 is contracted due to the negative pressure. The light emission opening 13 is open from the light emitting diode 21 toward the wounded part, and the light emitting diode 21 is disposed in the light emission opening 13. Accordingly, when the dressing body 10 is attached to the wounded part of a patient, only the dressing body 10 is contracted in the state that the light emitting diode 21 is disposed in the light emission opening 13, and the light emitting diode 21 is stably maintained without the change of the original position thereof. Accordingly, the contraction of the dressing body 10 is not interrupted and the light emitting diode 21 is not broken due to the contraction of the dressing body 10.

Figure 17A:
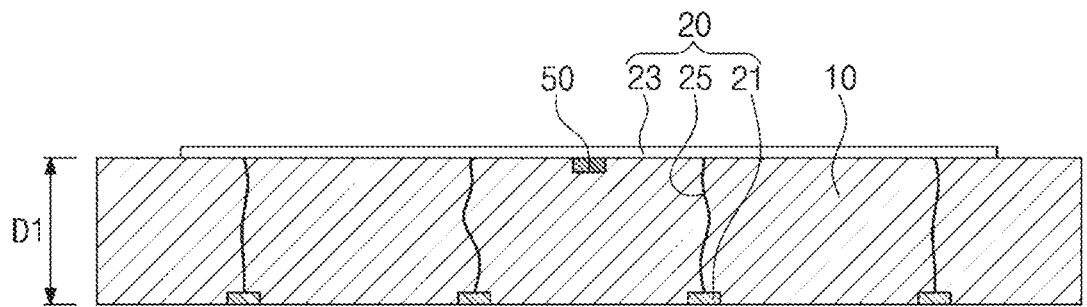
FIGS. 17A and 17B are cross-sectional views illustrating a dressing body and a light irradiation device in a dressing according to an embodiment of the present disclosure.
Figure 17B:
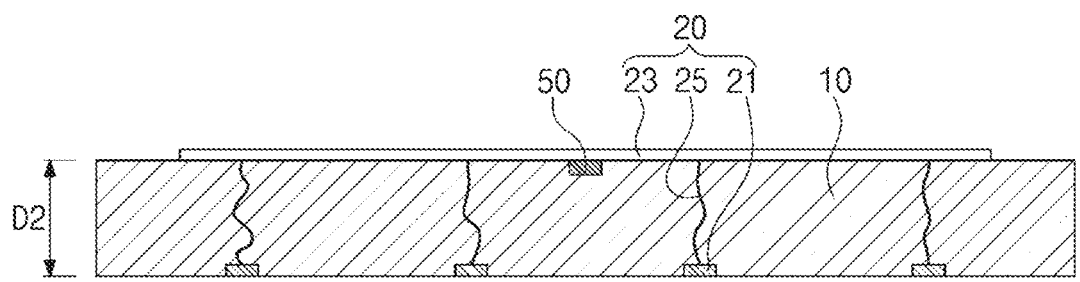

FIGS. 17A and 17B are cross-sectional views illustrating the dressing body 10 and the light irradiation device 20 in the dressing for negative pressure wound therapy according to an embodiment of the present disclosure.

Referring to FIGS. 17A and 17B, in the present embodiment, the light emitting diode 21 may be provided in the form of being spaced apart from the device board 23 through a separate power wiring 25 without being directly mounted on the device board 23. The light emitting diode 21 may be provided on the first plane of the dressing body 10. In other words, the device board 23 is disposed on the second plane of the dressing body 10, and the light emitting diode 21 is disposed on the first plane of the dressing body 10. In this case, the device board 23 and the light emitting diode 21 may be connected with each other through the power wiring 25 which is flexible.

When the device board 23 is connected with the light emitting diode 21 through the power wiring 25 which is flexible, even if negative pressure is applied into the inner space, the power wiring 25 flexibly copes with the negative pressure, like being bent. Accordingly, even if the thickness of the dressing body 10 is changed from the first thickness D1 to the second thickness D2, the light emitting diode 21 may be continuously disposed on the first plane along the surface of the first plane of the dressing body 10. The light emitting diode 21 is stably disposed on the surface of the dressing body 10, thereby minimizing that the light emitting diode 21 protrudes outward (that is, toward the wounded part of the patient) of the surface of the dressing body 10. If the light emitting diode 21 excessively protrudes toward the wounded part of the patent, the light emitting diode 21 presses the wounded part of the patient, so the patient may feel the inconvenience. In addition, as the light emitting diode 21 protrudes, the dressing body 10 may be separated from the wounded part of the patient. In this case, when the dressing body 10 is separated from the wounded part, the exudate may be less absorbed. However, in the present embodiment, the protrusion of the light emitting diode 21 is minimized to prevent the above problems.

As in the present embodiment, when the light emitting diode 21 is provided on a first substrate and the device board 23 is provided on the second plane, a part, which is covered by the device board 23, of the first plane of the dressing body 10 is minimized. Accordingly, a region, into which the exudate is absorbed through the first plane of the dressing body 10, of the dressing body 10 is maximized, thereby enhancing the efficiency of removing the exudate.

Figure 18:
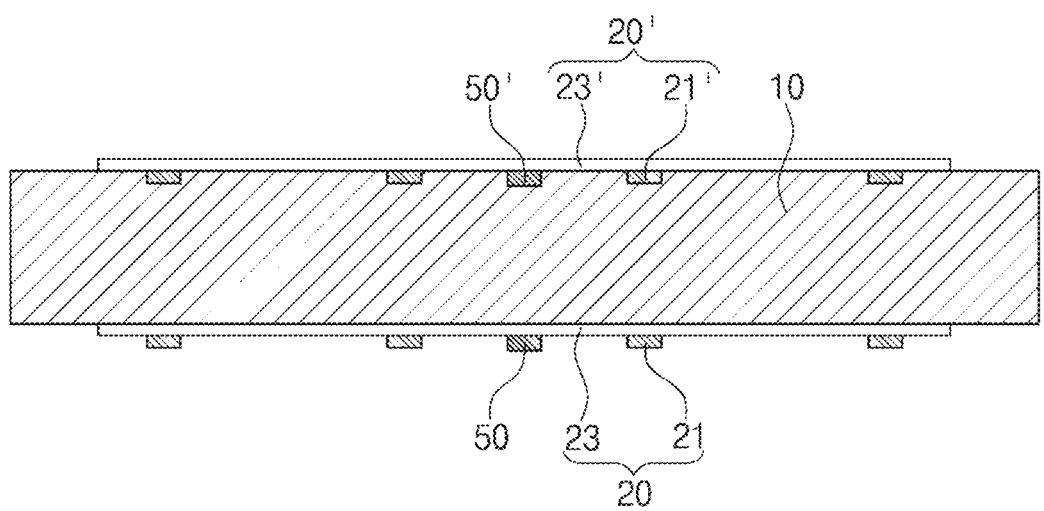
FIG. 18 is a cross-sectional views illustrating a dressing body and a light irradiation device in a dressing according to an embodiment of the present disclosure.

FIG. 18 is a cross-sectional view illustrating the dressing body 10 and the light irradiation device 20 in the dressing for negative pressure wound therapy according to an embodiment of the present disclosure.

Referring to FIG. 18, in the dressing for negative pressure wound therapy according to an embodiment of the present disclosure, a light irradiation device 20' may be further provided on the second plane of the dressing body 10, in addition to the light irradiation device 20 provided on the first plane of the dressing body 10. In the following description, the light irradiation device 20 provided on the first plane is referred to as the first light irradiation device, and the light irradiation device 20' provided on the second plane is referred to as the second light irradiation device, to distinguish between the light irradiation device 20 provided on the first plane and the light irradiation device 20' provided on the second plane, The second light irradiation device 20' is to apply light to the dressing body 10. As described above, the exudate is suctioned by the negative pressure pump, absorbed into the dressing body 10, and continuously retained in the dressing body 10 without a separate sterilizing process. Since the exudate has infectious bacteria removed from the wound part, the secondary infection may be caused due to the retained exudate. Accordingly, the exudate in the dressing body 10 needs to be separately sterilized. Therefore, the second light irradiation device 20' sterilizes the dressing body 10 to prevent the second infection.

The second light irradiation device 20' may include a device board 23' and a plurality of light emitting device chips 21'. The second light irradiation device 20' may be identical to the first light irradiation device 20, or different. In other words, the second light irradiation device 20' may employ light emitting device chips which are, in number, different from light emitting device chips of the first light irradiation device 20, and may include a light emitting diode to emit light of a wavelength which is different from the wavelength of light emitted from the first light irradiation device 20. In addition, the second light irradiation device 20' may be driven in the same manner as the manner of the first light irradiation device 20 or not driven in the same manner as the manner of the first light irradiation device 20. In addition, a pressure sensor may be additionally provided to clearly detect whether negative pressure is applied to the second light irradiation device 20'.

Although not illustrated, a light irradiation device may be further provided for another component to prevent secondary infection to be caused due to the exudate absorbed from the wounded part by the negative pressure pump. For example, the light irradiation device may be further provided in the tube, which connects the inner space with the negative pressure generating member, the tube connector, or the suction vessel. The additional light irradiation device is provided for the purpose of sterilization. Accordingly, the light irradiation device does not need to include a light emitting diode identical to the light emitting diode of the light irradiation device provided at a peripheral portion of the dressing body 10, but may include a light emitting diode to mainly emit sterilizing light such as UV light.

In the present embodiment, the light irradiation device to sterilize the exudate is further provided to sterilize (destroy bacteria included in) the suctioned exudate in real time, thereby effectively preventing the secondary infection due to the exudate.

In the dressing according to an embodiment of the present disclosure, only the second light irradiation device may be provided without the first light irradiation device.

Figure 19:
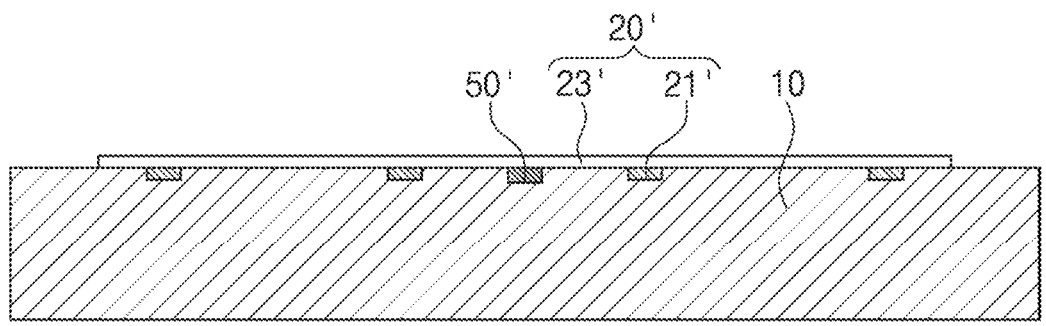
FIG. 19 is a cross-sectional view illustrating a dressing body and a light irradiation device, in a dressing according to an embodiment of the present disclosure.

FIG. 19 is a cross-sectional view illustrating the wounded part and the light irradiation device, in the dressing for negative pressure wound therapy according to an embodiment of the present disclosure.

Referring to FIG. 19, a light irradiation device 20' may be further provided on the second plane of the dressing body 10 in the dressing for negative pressure wound therapy according to an embodiment of the present disclosure.

The second light irradiation device 20' is to apply light to the dressing body 10. In the present embodiment, the second light irradiation device 20', which is to sterilize the exudate when the exudate is continuously retained in the dressing body 10 without being subject to an additional sterilizing process, may be used when the direct sterilization for the wounded part is not primarily required.

For example, when the exudate is retained in the dressing body 10 in the state that the direct sterilization for the wounded part is not required as the wounded part is cured to some extent, the second light irradiation device 20' may sterilize the inner part of the dressing, thereby preventing the secondary infection caused due to the exudate.

Figure 20:
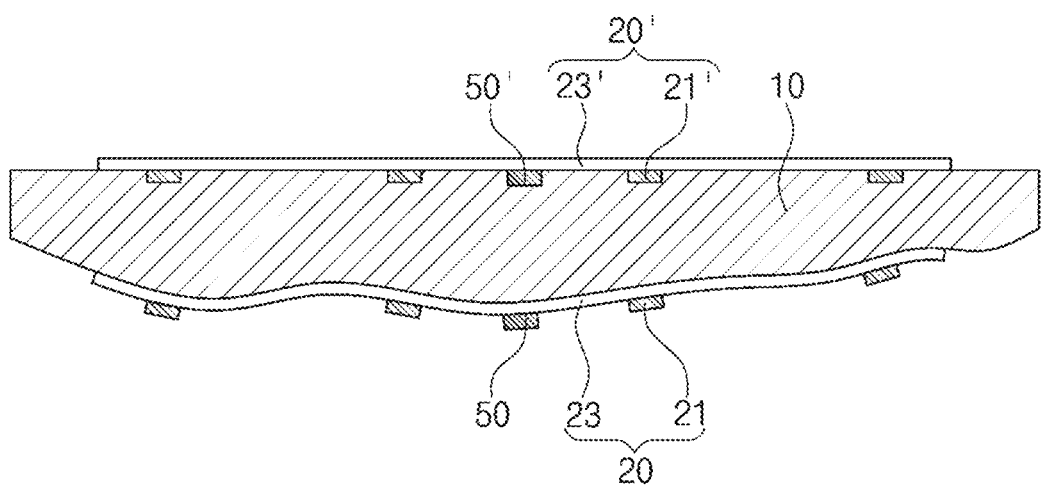
FIG. 20 is a cross-sectional view illustrating a dressing body and a light irradiation device in a dressing according to an embodiment of the present disclosure.

FIG. 20 is a cross-sectional view illustrating the dressing body 10 and the first and second light irradiation devices 20 and 20' in the dressing for negative pressure wound therapy according to an embodiment of the present disclosure, in which the dressing body 10 and the first and second light irradiation devices 20 and 20' are applied to the patient having a wounded part having an irregular surface.

Referring to FIG. 20, the first light irradiation device 20 provided on the first plane of the dressing body 10 may have flexibility. In particular, the device board 23 of the first light irradiation device 20 provided on the first plane may have flexibility. Accordingly, when the negative pressure is applied into the inner space, the dressing body 10 and the board of the first light irradiation device 20 may be deformed depending on the shape of the wounded part. Accordingly, the contact area between the surface of the wounded part and the first plane of the dressing is increased, thereby enhancing the effect of suctioning the exudate.

According to an embodiment of the present disclosure, a target requiring sterilization may be sterilized by applying a sterilizing light to the target. In particular, according to an embodiment of the present disclosure, the light irradiation device may be used to cure a wound. Accordingly, as described above, the light irradiation device may be used for dressing in the form including a light emitting diode. When a target to be sterilized is a human body and the skin of the human body is wounded, it is necessary to sterilize a pathogen at the wounded part. In this case, the pathogens refer to microorganisms such as bacteria, viruses, germs, fungi, protists, or molds. According to an embodiment of the present disclosure, the light irradiation device may be used for various wounds such as a wound, an ulcer, surgical site infection, a laceration, an incised wound, or a punctured wound.

Figure 21:
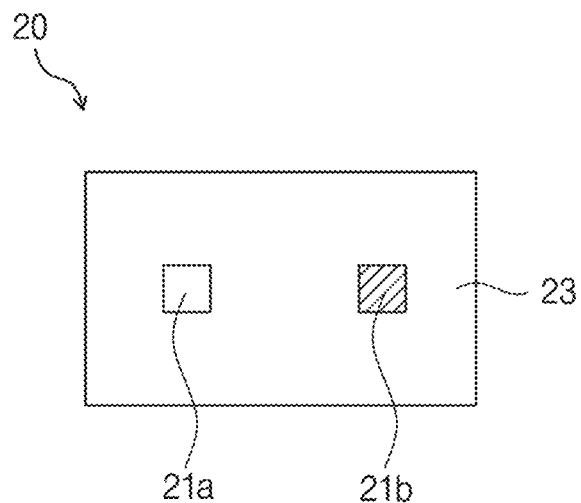
FIG. 21 is a plan view illustrating a light irradiation device, according to an embodiment of the present disclosure.

FIG. 21 is a plan view illustrating a light irradiation device, according to an embodiment of the present disclosure.

According to an embodiment of the present disclosure, a light irradiation device 20 includes a first light source 21a to emit first light, a second light source 21b to emit second light, and a substrate 23 to mount the first and second light sources 21a and 21b thereon.

Since the first light source 21a and the second light source 21b are mounted on the substrate 23, the substrate 23 is not limited to a specific form and may be provided in various forms sufficient to mount the first and second light sources 21a and 21b thereon or omitted. The substrate 23 may be provided in the form of including a wiring to supply power to the first and second light sources 21a and 21b. The substrate 23 may include, for example, a metallic substrate or a printed circuit board including the wiring.

The first light source 21a may emit first light in a blue wavelength band of a visible light wavelength band. The first light may correspond to light in a wavelength band of about 400 nm to about 500 nm. In one embodiment of the present disclosure, the first light may be light in a wavelength band of about 400 nm to about 420 nm. In one embodiment of the present disclosure, more specifically, the first light may be light having a wavelength of 405 nm.

The first light acts on a photosensitizer present in microorganisms such as bacteria, germs, and molds to damage the cell, thereby inducing the death of the microorganisms. The first light corresponds to the absorption wavelength of porphyrin, which is a photosensitizer present in bacteria. The first light exhibits higher sterilization power, particularly, in the wavelength range of 400 nm to 420 nm, more particularly, the wavelength range of 455 nm to 470 nm, which corresponds to the absorption wavelength band of the porphyrin, which is the photosensitizer. The porphyrin is a pigment that is essential for the process of intracellular oxygen transfer. The porphyrin exhibits a higher absorption, particularly, in the wavelength range of about 402 nm to about 420 nm, and more particularly absorbs a wavelength in the range of about 455 nm to 470 nm. In an embodiment of the present disclosure, since the content of the porphyrin varies depending on the type of bacteria, the porphyrin may be used for destroying specific bacteria by adjusting the wavelength and the intensity of the first light. When the first light is applied to bacteria, the porphyrin in the bacteria absorbs the first light, and reactive oxygen species are produced in the cell of the bacteria due to the energy of the first light. The reactive oxygen species are accumulated in cells of the bacteria to oxidize cell walls of the bacteria, thereby destroying the bacteria.

The second light source 21b emits the second light in the UV wavelength band. In other words, the second light may be light having a wavelength band in the range of about 100 nm to about 400 nm, and may be UVA, UVB, or UVC. The UVA may have a wavelength band in the range of about 315 nm to about 400 nm, the UVB may have a wavelength band in the range of about 280 nm to about 315 nm, and the UVC may have a wavelength band in the range of about 100 nm to about 280 nm. In an embodiment of the present disclosure, the second light may correspond to the UVC, and may have a wavelength band in the range of about 240 nm to about 280 nm. In an embodiment of the present disclosure, more specifically, the second light may be light having the wavelength of 275 nm.

When the second light is applied to bacteria, the DNA in the bacteria absorbs the second light, and the DNA structure is changed by the energy of the second light. The absorption of light by the DNA causes the binding of thymine and adenine in the DNA to be broken. This is because a base such as purine or pyrimidine, which constitutes the DNA, strongly absorbs UV light. As a result of light absorption, a thymine dimer is formed. This process leads to the DNA mutation, and the mutated DNA causes the death of the bacteria since the mutated DNA has no ability of cell proliferation. The DNA may absorb light having a wavelength band in the range of about 240 nm to about 280 nm.

Figure 22:
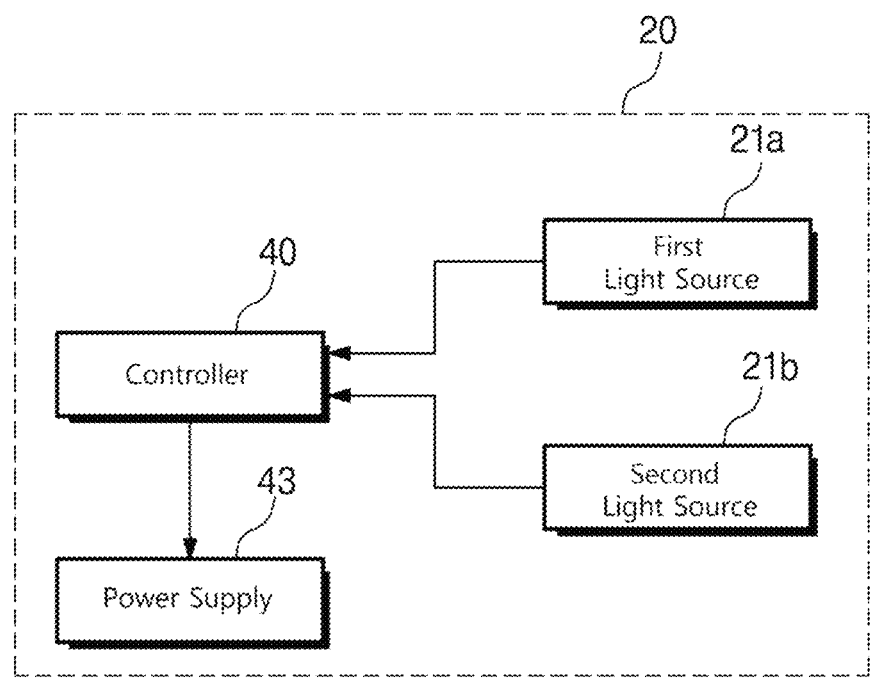
FIG. 22 is a block diagram illustrating a light irradiation device, according to an embodiment of the present disclosure.

FIG. 22 is a block diagram illustrating the light irradiation device, according to an embodiment of the present disclosure.

Referring to FIG. 22, according to an embodiment of the present disclosure, the light irradiation device 20 may include the first light source 21a to emit first light, the second light source 21b to emit second light, a controller 40 to control the first light source 21a and the second light source 21b such that the second light source 21b emits light after the first light source 21a emits light, and a power supply 43 to supply power to the controller 40 and the first and second light sources 21a and 21b.

Each of the first and second light sources 21a and 21b may emit the first light including a blue wavelength band and the second light including a UV wavelength band, as described above. In an embodiment of the present disclosure, the first and second light sources 21a and 21b may be implemented with various light sources. For example, each of the first and second light sources 21a and 21b may independently use various light sources such as a light emitting diode, a halogen lamp, a fluorescent lamp, a gas discharge lamp, or a laser, and the types of the light sources are not limited.

The controller 40 may control whether light is emitted from the first and second light sources 21a and 21b, an amount of the light, the intensity of the light, or time in which the light is emitted. The controller 40 may control whether the light is emitted, an amount of the light, the intensity of the light, or a light emitting duration, through various manners.

The power supply 43 is electrically connected with the first and second light sources 21a and 21b and the controller 40 to supply power to the first and second light sources 21a and 21b and the controller 40. Although drawings illustrate that the power supply 43 supplies power to the first and second light sources 21a and 21b and the controller 40, the present disclosure is not limited thereto. For example, the power supply 43 may be directly connected with the first and second light sources 21a and 21b to supply power to the first and second light sources 21a and 21b.

The light irradiation device 20 may further include an optical unit to selectively collect or radiate light emitted from the first and second light sources 21a and 21b. The optical unit may include at least one lens, and the lens may perform various functions of focusing, dispersing, homogenizing, or non-homogenizing light from the first and second light sources 21a and 21b.

In the present embodiment, the controller 40 simultaneously or individually drives the first light source 21a and the second light source 21b. In other words, the first and second light sources 21a and 21b may be turned on/off simultaneously or individually. In addition, even the intensities of light, that is, the first light and the second light emitted from the first and second light sources 21a and 21b may be simultaneously or individually controlled.

In an embodiment of the present disclosure, the controller 40 may allow a daily irradiation amount to be 3 mJ/cm² or less. In particular, in the case of UVC, the controller 40 maintains the daily irradiation amount to be 3 mJ/cm² or less. Further, in the case of UVA, when a daily irradiation time is less than 1,000 seconds, the daily irradiation amount is maintained such that the daily irradiation amount does not exceed 1 J/cm², and when the daily irradiation time is equal to or greater than 1,000 seconds, the daily irradiation amount is maintained such that the daily irradiation amount does not exceed 1 mW/cm².

In an embodiment of the present disclosure, the distance from the first and second light sources 21a and 21b to a target to be sterilized may be variously set. For example, the distance may be variously changed depending on the intensities of light from the first and second light sources 21a and 21b, the type of the target to be sterilized, an area or a volume to be sterilized, or a target material (for example, germs or bacteria) to be sterilized. Similarly, in an embodiment of the present disclosure, timings and/or durations in which light from the first light source 21a and the second light source 21b is irradiated may be variously set.

Figure 23A:
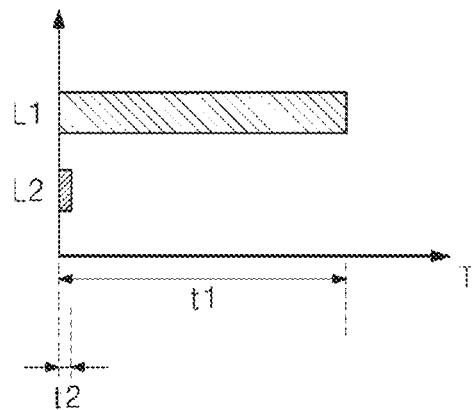
FIGS. 23A to 23C illustrate a method for driving a light irradiation device, according to an embodiment of the present disclosure, and illustrates times based on turning on/off the first and second light sources.
Figure 23B:
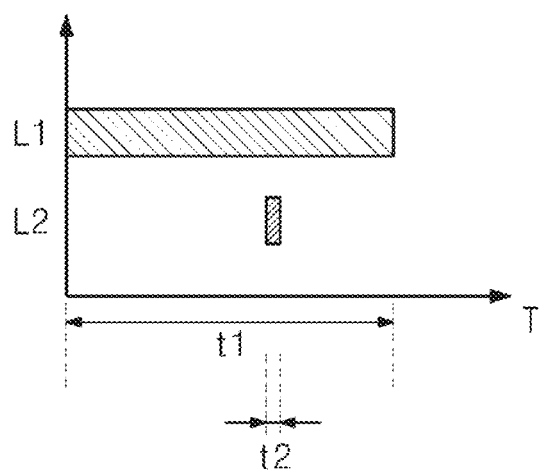
Figure 23C:
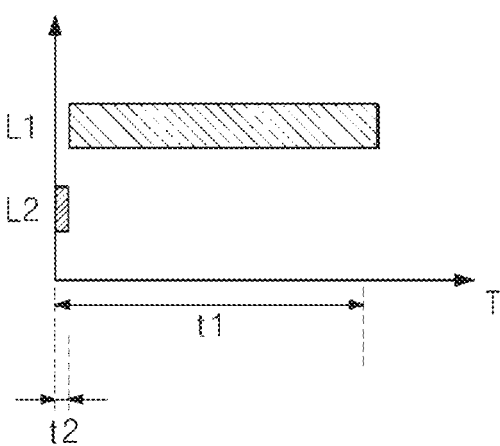

FIGS. 23A to 23C illustrate a method for driving a light irradiation device, according to an embodiment of the present disclosure, and illustrates times based on turning on/off the first and second light sources;

According to an embodiment of the present disclosure, in the light irradiation device 20, the first light is assigned with "L1", the second light is assigned with "L2", and elapsed time is assigned with "T", the first light source 21a is turned on for a first duration t1 to emit the first light L1, and the second light source 21b is turned on for a second duration t2 to emit the second light L2. In the present embodiment, the first duration t1 in which the first light L1 is irradiated may be longer than the second duration t2 in which the second light L2 is irradiated. Since the second light L2 exerts a great influence on, especially, a human body, the second light L2 may be irradiated for a shorter duration than the irradiation duration of the first light L1. For example, the first light L1 may be applied for about 10 minutes, and the second light L2 may be applied for less than about 10 seconds.

The irradiation durations t1 and t2 of the first light L1 and the second light L2 emitted from the first and second light sources 21a and 21b, and amounts of the first light L1 and the second light L1 in irradiation may be variously changed, but a total dose applied to the target to be sterilized may be set to a value harmless to the human body. In particular, a dose per day, which is in a harmless range, is an allowable dose when the second light L2 is applied to the human body, and the second light source 21b may emit the second light L2 in less than the allowable dose. The dose may vary depending on the harmfulness of the light emitted from the first light source 21a and the second light source 21b. In an embodiment of the present disclosure, the dose of the second light source 21b may be less than 1/10 of the dose of the first light source 21a, and, according to another embodiment, may be 1/20 of the dose of the first light source 21a. For example, the allowable dose of the second light L2 may be in the range of about 30 J/m² to about 1,000,000 J/m².

As illustrated in FIG. 23A and FIG. 23C, the first light L1 and the second light L2 may start to irradiate simultaneously or at mutually different timings. When the first light L1 and the second light L2 may start to irradiate at mutually different timings, the first light L1 may first irradiate or the second light L2 may first irradiate. The duration in which the first light L1 and the second light L2 irradiate may overlap with each other or may not overlap. When the duration, for which the first light L1 and the second light L2 irradiate, does not overlap with each other, the interval between the timings at which the first light L1 and the second light L2 are applied may be set to be a shorter time interval. For example, the interval between the timings at which the first light L1 and the second light L2 are applied may be within several hours, several minutes, or several seconds.

The sterilizing device according to an embodiment of the present disclosure exhibits a sterilization effect higher than the individual sterilization effect by the first light L1 or the individual sterilization effect by the second light L2, due to the synergic effect that may be obtained as the first light and the second light are applied simultaneously or within timings close to each other.

According to an embodiment of the present disclosure, the sterilizing device employs the sterilization principle of the first light of generating reactive oxygen species due to a photosensitizer and the second light of causing the damage to DNA by obtaining a thymine dimer. In an embodiment of the present disclosure, the significantly high sterilization effect may be obtained within a shorter time even with a smaller amount of energy by using the first light source and the second light source, as compared to the case of an individual use of the first and second light sources The bacteria having received chemical and physical stresses may be rapidly increased in a death rate even by a weak stimulus additionally applied thereto. Accordingly, in an embodiment of the present disclosure, mutually different two sterilizing mechanisms based on the first light and the second light, which correspond to blue light and UV light, apply mutually different stresses to the bacteria. Accordingly, the synergy effect of the stresses may destroy the bacteria with a smaller amount of energy as compared to the individual use of the two light sources. According to an embodiment of the present disclosure, the second light is irradiated in amount harmless to a biological tissue of the target, which is to be sterilized, while being applied together with the first light. Accordingly, the sterilization synergy effect may be obtained by two light sources, so the present disclosure may produce the effective sterilization effect within a shorter time without the damage to a human tissue, when the target to be sterilized is a human body.

To the contrary, the use of only the first light is not harmful to the human body, but the sterilization power is weak. Accordingly, the first light needs to be irradiated with higher energy for a longer time. It should be noticed that the use of only the second light produces excellent sterilization power, but is harmful to the human body.

As described above, in an embodiment of the present disclosure, the sterilizing device may be used to sterilize various pathogens. Particularly, according to an embodiment of the present disclosure, the light irradiation device 20 may be used for sterilizing infectious bacteria in the initial stage by irradiating sterilizing light to an acute infected wound, and thus, the period for curing the wound may be shortened. For the acute wound, reducing the number of infectious bacteria in the initial stage of the wound is the most important in the process of curing the wound. When the initial sterilization is not sufficiently performed with respect to the acute wound, the curing of the cut wound is not performed normally, so the cut wound may develop into a chronic cut would that is not cured for 3 months or longer. However, when the infectious bacteria are sterilized in the initial stage using the light irradiation device 20 according to the embodiment of the present disclosure, the chronic cut would may be prevented.

In addition, microorganisms, such as bacteria, germs, and molds, present on animals and various articles may be sterilized in addition to the human body. Accordingly, the target to be sterilized by the sterilizing device according to an embodiment of the present disclosure is not limited to a human body, but may be expanded to animals and various articles.

According to the embodiment of the present disclosure, as described, above, the sterilization effect may be significantly increased when the first light and the second light emitted from the first light source 21a and the second light source 21b are applied simultaneously or within timings close to each other. In addition, according to an embodiment of the present disclosure, when the first light and the second light are sequentially irradiated, the significantly higher sterilization effect may be obtained as compared to that the second light and the first light are sequentially irradiated. Accordingly, according to an embodiment of the present disclosure, the sterilization effect may be maximized through sequentially applying the first light and the second light to the target to be sterilized.

According to an embodiment of the present disclosure, the first light is applied to the target to be sterilized for a specific time before the second light is irradiated, and then the second light is irradiated. Accordingly, DNA is prevented from being recovered from the damage again after the first light is first irradiated. Accordingly, the significantly higher sterilization effect may be obtained even with a smaller dose as compared to the case that the first light is individually irradiated.

In an embodiment of the present disclosure, when the second light is emitted sequentially after the first light, in addition to the first light, an amount of the second light needs to be controlled. In an embodiment of the present disclosure, the synergic effect of sterilization may be obtained and an influence on the human body may be minimized by sequentially irradiating the first light and the second light. To this end, when the first light source 21a and the second light source 21b are turned on/off, a manner of continuously emitting light, a manner of sequentially increasing or decreasing the intensity of light, a flickering manner, or a manner of mixing the above manners may be employed.

Figure 24A:
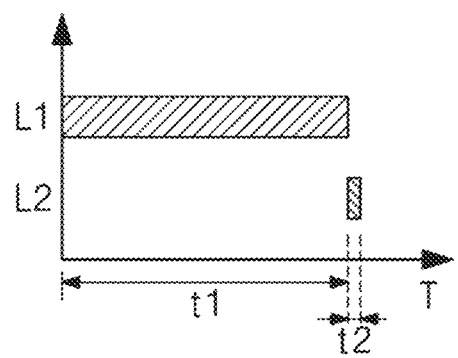
FIGS. 24A and 24B are views illustrating a method for driving a light irradiation device, according to an embodiment of the present disclosure, when first light and second light are sequentially irradiated, and illustrates times based on turning on/off the first and second light sources.
Figure 24B:
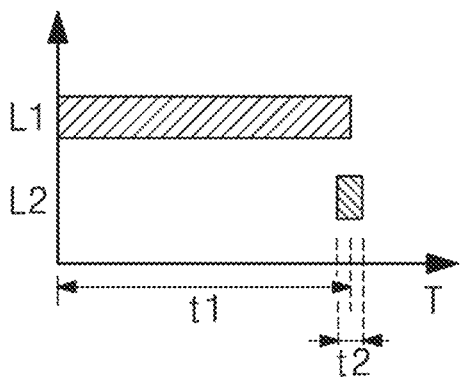

FIGS. 24A and 24B are views illustrating a method for driving the light irradiation device according to an embodiment of the present disclosure, when the first light and the second light are sequentially irradiated, and illustrates times based on turning on/off the first and second light sources.

Referring to FIGS. 24A and 24B, in an embodiment of the present disclosure, the first light L1 may be first irradiated, and then the second light L2 may be irradiated. When the first light L1 is first irradiated and then the second light L2 is irradiated, the sterilization effect is significantly increased as compared to the case that the second light is first irradiated and then the first light L1 is irradiated. When the second light L2 is first irradiated and the first light L1 is later irradiated, the effect of inhibiting the proliferation of bacteria by the second light L2 may be reduced by irradiating the first light L1. Accordingly, even if the structure of DNA is partially mutated by the second light L2, the mutated DNA is subject to photoreactivation by irradiating the first light L1. The bacteria recovered through the irradiation of the first light L1 return to a state in which the bacteria may be proliferated. Accordingly, although the total sterilization power is still excellent, the sterilization power in the final stage may be more reduced as compared to the case that the first light L1 and the second light L2 are sequentially irradiated.

Alternatively, when the first light L1 is applied to the target to be sterilized and then the second light L2 is sequentially applied to the target to be sterilized by using the light irradiation device 20 according to an embodiment of the present disclosure, reactive oxygen species are generated in bacteria by the first light L1, which is first irradiated, so oxidative stress is caused in bacteria. In this state, since additional sterilization is performed by the second light L2 irradiated later, the death degree of the bacteria is significantly increased even in a smaller irradiation amount.

In this embodiment, the timing at which the second light L2 is applied may vary under the condition that the first light L1 and the second light L2 are sequentially applied. For example, irradiation of the second light L2 may start after the irradiation of the first light L1 is finished as illustrated in FIG. 3A, and as illustrated in FIG. 3B, the irradiation of the second light L2 may start even though the irradiation of the first light L1 is not completed. In this case, since the timings at which the first light L1 and the second light L2 start irradiating may partially overlap with each other, the durations of the first time and the second time may mutually overlap.

As described above, the light irradiation device 20 according to an embodiment of the present disclosure may be driven by the controller 40 under the condition that the first light L1 and the second light L2 are sequentially irradiated.

Figure 25A:
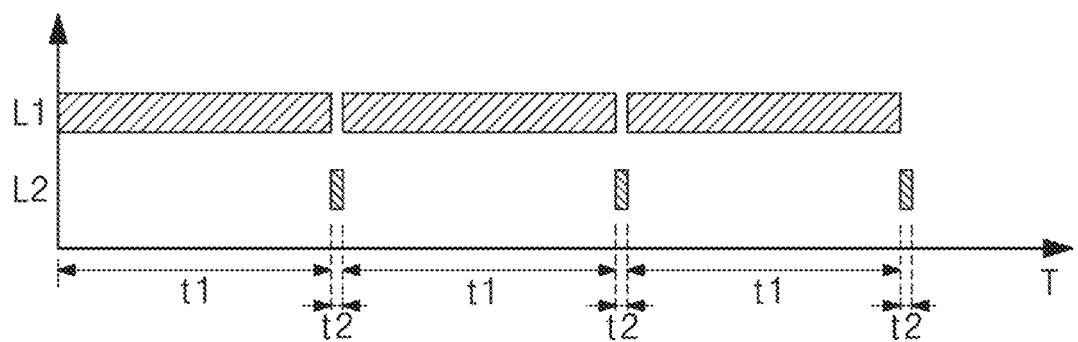
FIGS. 25A to 25C illustrate a method for driving a light irradiation device, according to an embodiment of the present disclosure, and illustrates times based on turning on/off the first and second light sources.
Figure 25B:
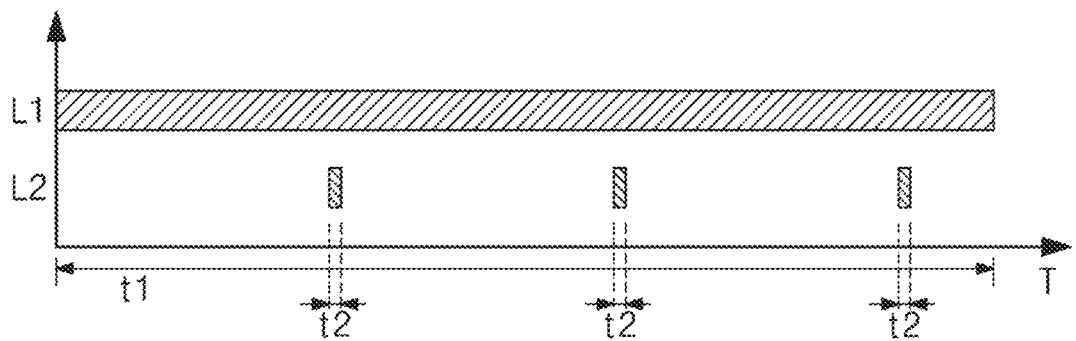
Figure 25C:
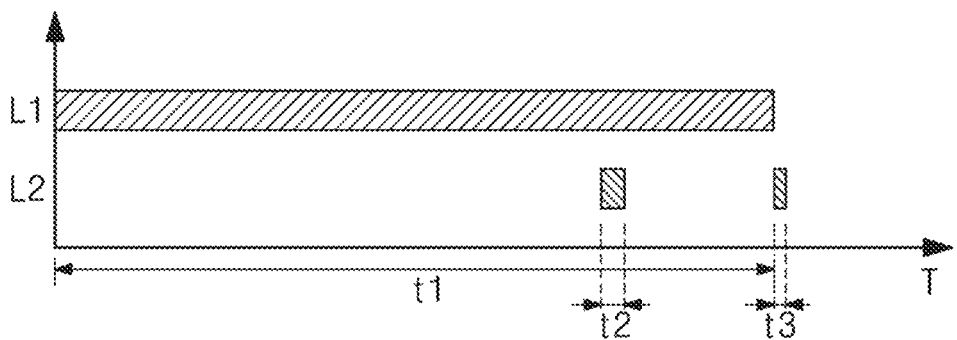

FIGS. 25A to 25C illustrate a method for driving a light irradiation device, according to an embodiment of the present disclosure, and illustrates times based on turning on/off the first and second light sources;

Referring to FIG. 25A, the first light L1 and the second light L2 may be periodically irradiated to the target to be sterilized. In other words, the first light L1 is irradiated to the target to be sterilized for the first time t1, and the second light L2 is irradiated to the target to be sterilized for the second time t2. Then, irradiation of the first light L1 and the second light L2 is repeated. The repeat period and the repeat count may vary depending on the type of the target to be sterilized and the total amount of the target to be sterilized. In this case, the repeat period and the repeat count of the first light L1 and the second light L2 may be determined such that the total dose of the first light L1 and the total dose of the second light L2 become values equal to or less than the allowable dose for the human body.

Referring to FIG. 25B, when the first light L1 and the second light L2 are applied, the first light L1 may be continuously applied to the target to be sterilized without interruption under the condition that the second light L2 is applied after the first light L1 is applied. To the contrary, the second light L2 is not continuously applied, but discontinuously applied while being superposed with the first light L1.

As illustrated in drawings, the first light L1 may be continuously applied to the target to be sterilized for the first time t1 without interruption, and the second light L2 may be applied to the target to be sterilized for the second time t2 during the continuous application of the first light L1, after the first light L1 is applied to some extent. The second light L2 may be continuously repeatedly applied to the target to be sterilized.

Referring to FIG. 25C, when the first light L1 and the second light L2 are applied, the first light L1 may be continuously applied to the target to be sterilized without interruption or may be stopped before the second light L2 is applied, under the condition that the second light L2 is applied after the first light L1 is applied. As illustrated in drawings, when the first light L1 is applied to the target to be sterilized for the first time t1, the second light L2 may be applied for the second time t2 during the application of the first light L1. Thereafter, after the application of the first light L1 is finished, the second light L2 may be applied for a third time t3. In this case, regarding the application time of the second light L2, the second light L2 may be applied to the target to be sterilized for mutually different time within an allowable dose permitted as being safe for a human body. In other words, the second time t2 and the third time t3 in which the second light L2 is applied may have mutually different values.

In an embodiment of the present disclosure, when the second light L2 is applied as soon as the first light L1 is applied and stopped, the highest sterilization effect may be exhibited, and the second light L2 may be sequentially applied without interruption in the state the first light L1 is applied. However, instead of that the second light L2 is applied as soon as the first light L1 is applied and stopped, time may be slightly elapsed after the first light L1 is applied and stopped and then the second light L2 may be applied. In this case, the elapsed time interval may be significantly short. Meanwhile, when the sterilization effect is obtained as the first light L1 and the second light L2 are sequentially applied, the next sequential irradiation of the first light L1 and the second light L2 may be performed after a sufficient amount of time is elapsed.

Figure 26A:
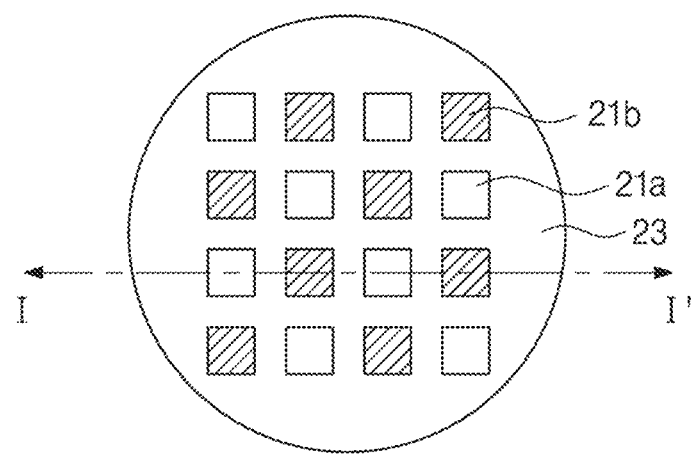
FIG. 26A is a plan view of the light irradiation device according to an embodiment of the present disclosure.

According to an embodiment of the present disclosure, the light irradiation device 20 may be implemented in various forms. FIG. 26A is a plan view of the light irradiation device 20 according to an embodiment of the present disclosure, and FIG. 26B is a sectional view taken along line I-I' of FIG. 26A.

Figure 26B:
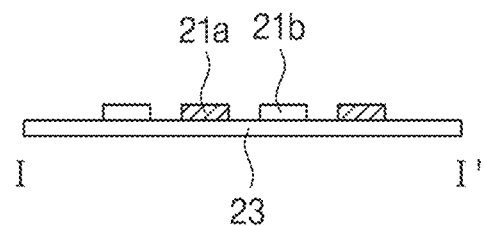
FIG. 26B is a sectional view taken along line I-I' of FIG. 26A.

Referring to FIGS. 26A and 26B, according to an embodiment of the present disclosure, the light irradiation device 20 may include the first light source 21a, the second light source 21b, and the substrate 23 on which the first light source 21a and the second light source 21b are mounted.

In the present embodiment, a plurality of first light sources 21a may be provided, and a plurality of second light sources 21b may be provided. For example, the first light sources 21a and the second light sources 21b may be provided in equal numbers and may be alternately arranged in the form of a matrix as illustrated in FIG. 26A. However, the number of the first and second light sources 21a and 21b is not limited thereto, and the number of the first light sources 21a may be smaller than the number of the second light sources 21b. In addition, according to an embodiment of the present disclosure, the first light sources 21a and the second light sources 21b may be regularly, or irregularly arranged depending on the number of the first light sources 21a and the number of the second light sources 21b.

According to an embodiment of the present disclosure, the light irradiation device 20 may further include a housing to receive the first and second light sources 21a and 21b and the substrate 23. The housing may have a transmission window to transmit light emitted from the first and second light sources 21a and 21b and the light emitted from the first and second light sources 21a and 21b may be provided to the human body through the transmission window.

In an embodiment of the present disclosure, the controller 40 may be provided in various forms on the substrate 23. For example, the controller 40 may be provided in the form of a separate circuit wiring or in the form of a separate chip, to be mounted on the substrate 23.

The light irradiation device may be implemented in various forms and used for various purposes. For example, according to an embodiment of the present disclosure, the light irradiation device may be applied to various places requiring lighting and sterilizing, and may be used as, especially, a medical dressing. For example, the light irradiation device may be used in medical facilities such as operating rooms or hospitals or used for curing a patient in a place requiring public hygiene or personal hygiene, especially, for disinfecting or sterilizing a wound.

According to the present disclosure, the light irradiation device may be applied to public facilities, a public space, and a product for common use for treatment purposes, or may be applied to private facilities, a personal space, and a persona use product to be used for personal treatment purposes.

As described above, according to an embodiment of the present disclosure, the sterilizing device may be applied to various other devices requiring sterilizing, and particularly, may be applied to a device using a light source. In addition, the sterilizing device may be used as a lighting device in addition to the intrinsic function thereof. For example, according to an embodiment of the present disclosure, the sterilizing device may further include an additional light source for lighting a specific space. In this case, the additional light source may emit light in a visible wavelength band. The additional light source may emit light corresponding to the entire spectrum of the visible light area, or may emit light corresponding to the spectrum of a specific color.

Alternatively, in an embodiment of the present disclosure, the first light source 21a may emit light in the visible light wavelength band including light in the blue wavelength band without an additional light source. For example, the first light source 21a emits light in a wavelength band in the range of about 380 nm to about 750 nm, and most of the light corresponds to a visible light wavelength band. In this case, the first light source 21a may totally provide light in the visible light wavelength band while providing light in the blue wavelength band for obtaining a synergic effect through the combination with the second light source 21b, thereby obtaining the sterilization effect as in embodiments described above. In this manner, when an additional light source is provided to emit light in the visible light wavelength band, or the first light source emits the light in the visible light wavelength band, the light may have the spectrum similar to that of sunlight. The light having the spectrum similar to that of sunlight may exhibit the effect similar to being frequently exposed to sunlight. Accordingly, the synthesis of vitamin D may be facilitated or the prevalence ratio of illnesses such as nearsightedness may be lowered.

Hereinafter, an experimental example of the sterilization effect of the light irradiation device according to an embodiment of the present disclosure will be described.

Experimental Example 1—Individual Sterilization Power Test of First Light and Second Light In the present test, an MRSA strain was used as a pathogen. After the MRSA strain was cultured, a suspension having a constant bacteria concentration (7 log) was prepared. The first light and the second light were irradiated to the bacteria suspension in each light amount. In this case, the wavelength of the first light was 405 nm and the wavelength of the second light was 275 nm. The bacteria irradiated with the first light and the second light were each diluted at a specific concentration, inoculated into agar plates, and then cultured again. Thereafter, the number of colonies of the cultured bacteria was identified, and the numerical value was converted into a log value. Each test was performed under the same conditions five times.

Figure 27A:
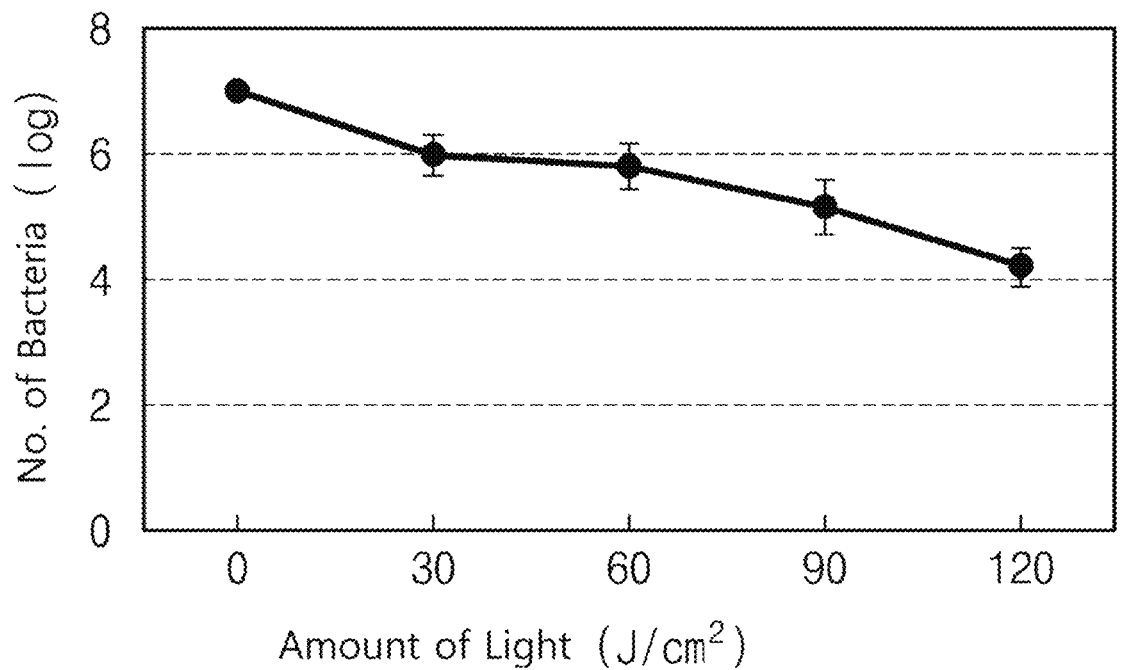
FIG. 27A is a graph illustrating a test result of sterilization power of first light.
Figure 27B:
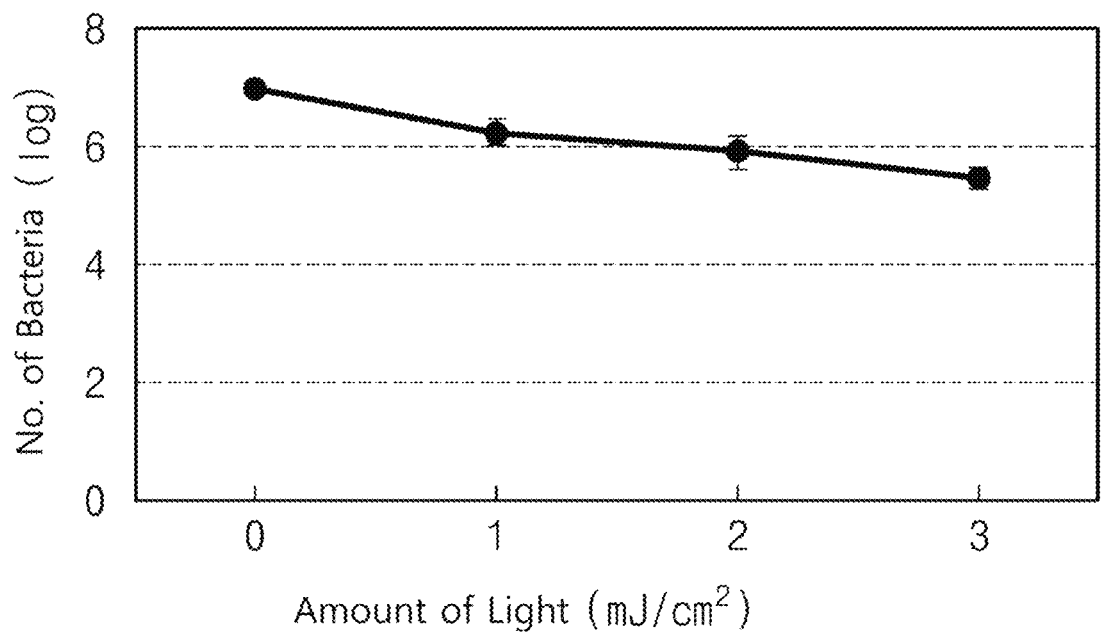
FIG. 27B is a graph illustrating a test result of sterilization power of second light.

Table 1 and FIG. 27A illustrate the test result for the sterilization power of the first light, and Table 2 and FIG. 27B illustrate the test result for the sterilization power of the second light.

TABLE 1

|  | Light amount (J/cm$^2$) | | | | |
| --- | --- | --- | --- | --- | --- |
|  | 0 | 30 | 60 | 90 | 120 |
| The number of bacteria | 7.00 | 5.97 | 5.78 | 5.15 | 4.17 |
| Error | 0.00 | 0.32 | 0.35 | 0.43 | 0.29 |

It may be recognized from Table 1 and FIG. 27A that, as an amount of the first light, which is irradiated, is increased, the number of the bacteria is reduced. It is clear that the number of bacteria is reduced even if the margin of error is considered.

TABLE 2

|  | Light amount (J/cm$^2$) | | | |
| --- | --- | --- | --- | --- |
|  | 0 | 1 | 2 | 3 |
| The number of bacteria | 7.00 | 6.23 | 5.88 | 5.45 |
| Error | 0.00 | 0.23 | 0.27 | 0.18 |

It may be recognized from Table 2 and FIG. 27B that, as an amount of the second light, which is irradiated, is increased, the number of the bacteria is reduced. It is clear that the number of bacteria is reduced even if the margin of error is considered. In addition, it is recognized that the second light sterilizes the bacteria in amount smaller than an amount of the first light.

Experimental Example 2—Sterilization Power Test in Combination of First Light and Second Light In the present test, an MRSA strain was used as a pathogen. After the MRSA strain was cultured, a suspension having a constant bacteria concentration (7 log) was prepared. The individual irradiation of the first light, the individual irradiation of the second light, and the combination of the first light and the second light were performed with respect to the bacteria suspension. Comparative example 1 illustrates that non-light is irradiated to the bacteria suspension, Comparative example 2 illustrates that the second light was individually irradiated to the bacteria suspension, Comparative example 3 illustrates that the first light was individually irradiated to the bacteria suspension, and Embodiment illustrates that the combination of the first light and the second light was irradiated to the bacteria suspension. In this case, the wavelength of the first light was 405 nm, the dose of the first light was 120 J/cm$^2$, and the wavelength of the second light was 275 nm, and the dose of the second light was 3 mJ/cm$^2$. In Embodiment, the second light was irradiated in the dose of 3 mJ/cm$^2$ and then the first light was irradiated in the dose of 120 J/cm$^2$. Next, in Comparative Examples 1 to 3 and Embodiment, the bacteria were diluted at a constant concentration, inoculated into agar plates, and then cultured again. Thereafter, the number of colonies of the cultured bacteria was identified, and the numerical value was converted into a log value.

Each test was performed under the same conditions five times.

Figure 28A:
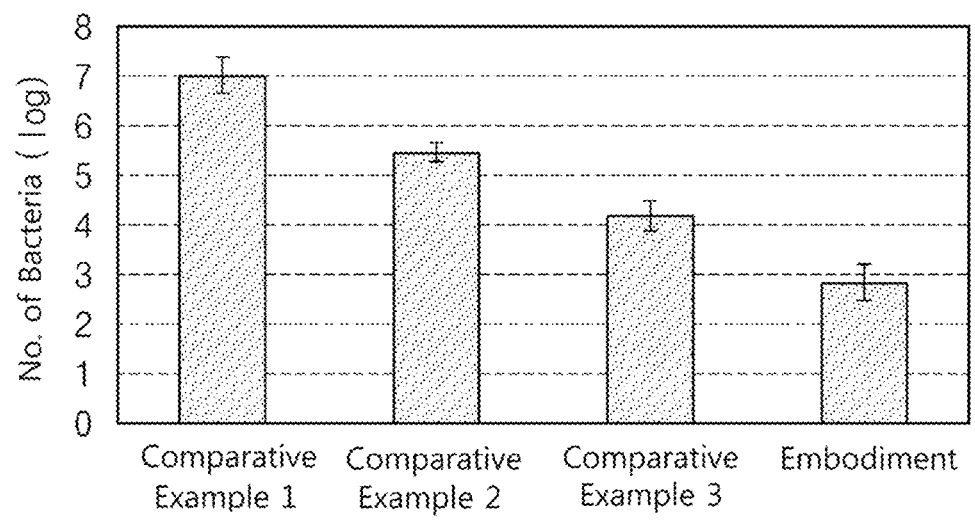
FIG. 28A illustrates the number of bacteria when first light is individually irradiated, when second light is individually irradiated, and when the first light and the second light are combined to be irradiated.
Figure 28B:
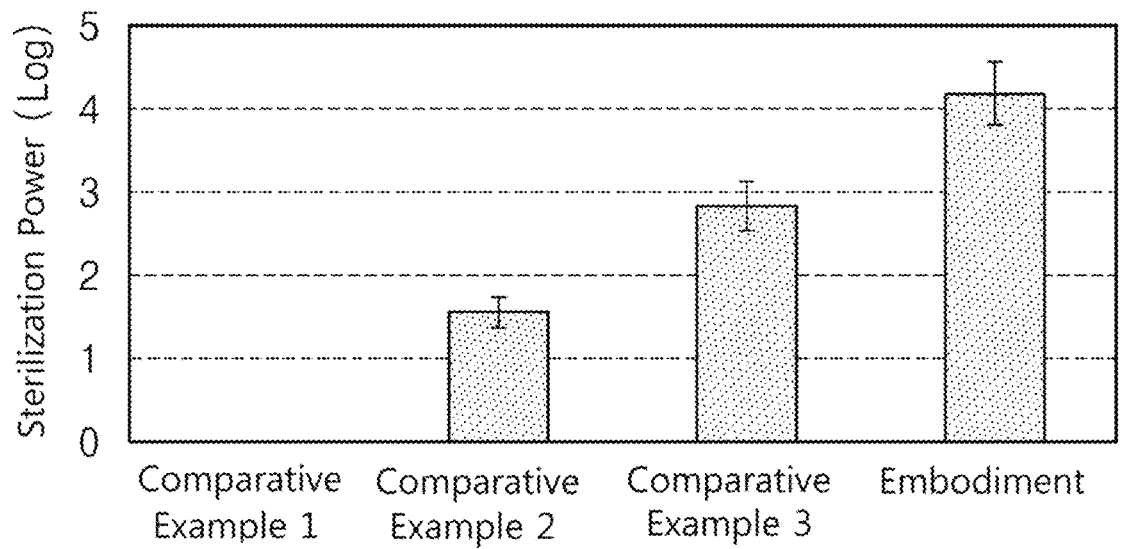
FIG. 28B illustrates sterilization power when first light is individually irradiated, when second light is individually irradiated, and when the first light and the second light are combined to be irradiated.

FIG. 28A and Table 3 illustrate the number of bacteria in the individual irradiation of the first light, the individual irradiation of the second light, and the irradiation of the combination of the first light and the second light. FIG. 28B and Table 4 illustrate the sterilization power in the individual irradiation of the first light, the individual irradiation of the second light, and the irradiation of the combination of the first light and the second light.

TABLE 3

|  | Light condition | | | |
| --- | --- | --- | --- | --- |
|  | Comparative Example 1 | Comparative Example 2 | Comparative Example 3 | Embodiment |
| The number of bacteria | 7.00 | 5.45 | 4.17 | 2.83 |
| Error | 0.00 | 0.18 | 0.29 | 0.37 |

TABLE 4

|  | Light condition | | | |
| --- | --- | --- | --- | --- |
|  | Comparative Example 1 | Comparative Example 2 | Comparative Example 3 | Embodiment |
| Sterilization power | 0.00 | 1.55 | 2.83 | 4.17 |
| Error | 0.00 | 0.18 | 0.29 | 0.37 |

Referring to FIGS. 28A, 28B, Table 3, and Table 4, about 90% of sterilization power was illustrated in the individual irradiation of the second light, about 99% of sterilization power was illustrated in the individual irradiation of the first light, and 99.99% or more of sterilization power was illustrated in irradiation of the combination of the first light and the second light. Accordingly, it may be recognized that an amount of bacteria is significantly reduced, and thus the sterilization power is significantly increased when the combination of the first light and the second light is irradiated, as compared to when the light is not irradiated, and to when the first light or the second light is individually irradiated.

Experimental Example 3—Test for Variation in Sterilization Power Based on Sequence of Combining First Light and Second Light In the present test, an MRSA strain was used as a pathogen. After the MRSA strain was cultured, a suspension having a constant bacteria concentration (7 log) was prepared. After the second light was irradiated to the bacteria suspension, the first light was irradiated to the bacteria suspension. In addition, the second light was irradiated to the bacteria suspension after the first light was irradiated to the bacterial suspension. Comparative example 1 illustrates that non-light was irradiated to the bacteria suspension, Embodiment 1 illustrates that the first light was irradiated to the bacteria suspension after the second light was irradiated to the bacteria suspension, and Embodiment 2 illustrates that the second light was irradiated to the bacteria suspension after the first light was irradiated to the bacteria suspension.

In Embodiment 1, after the second light having the wavelength of 275 nm was irradiated to the bacteria suspension with a dose of 3 mJ/cm$^2$, the first light having the wavelength of 405 nm was irradiated to the bacteria suspension with a dose of 120 J/cm$^2$. In Embodiment 2, after the first light having the wavelength of 405 nm was irradiated to the bacteria suspension with a dose of 120 J/cm$^2$, the second light having the wavelength of 275 nm was irradiated with the dose of 3 mJ/cm$^2$.

Next, in Comparative Example, Embodiment 1, and Embodiment 2, the bacteria were diluted at a constant concentration, inoculated into agar plates, and then cultured again. Thereafter, the number of colonies of the cultured bacteria was identified, and the numerical value was converted into a log value.

Each test was performed under the same conditions five times.

Figure 29A:
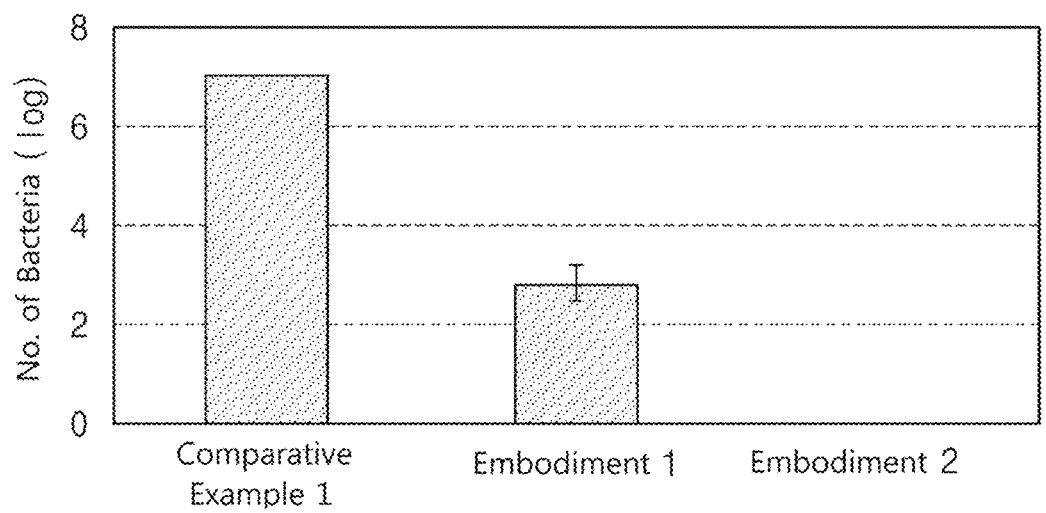
FIG. 29A illustrates the number of bacteria irradiated with light obtained by differently setting the sequence of combining first light and second light.
Figure 29B:
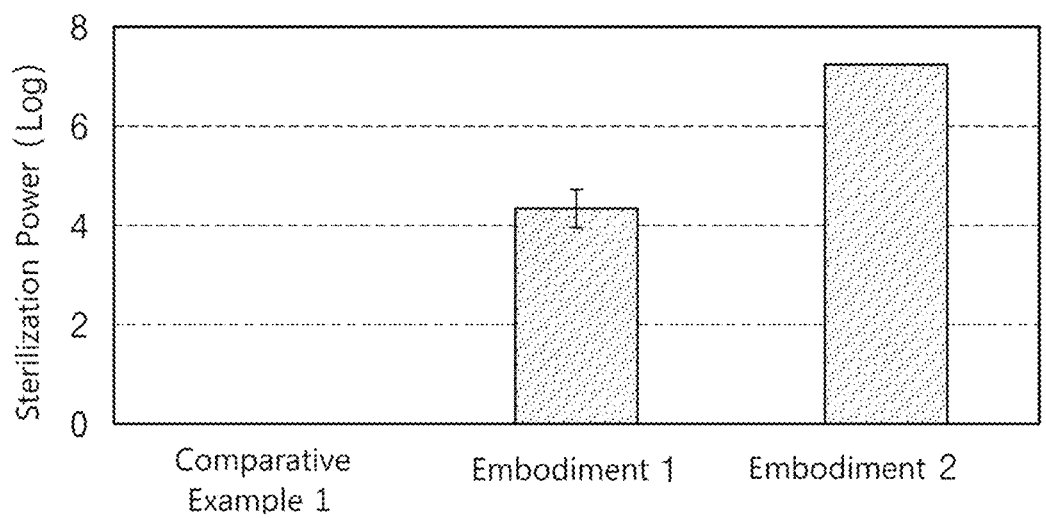
FIG. 29B illustrates sterilization power obtained by differently setting the sequence of combining the first light and the second light.

FIG. 29A and Table 5 illustrate the number of bacteria when the sequence of combining the first light and the second light is differently set, and FIG. 29B and Table 6 illustrate the sterilization power when the sequence of combining the first light and the second light is differently set.

TABLE 5

| | Light condition | | |
|---|---|---|---|
| | Comparative Example | Embodiment 1 | Embodiment 2 |
| The number of bacteria | 7.00 | 2.83 | 0.00 |
| Error | 0.00 | 0.37 | 0.00 |

TABLE 6

| | Light condition | | |
|---|---|---|---|
| | Comparative Example | Embodiment 1 | Embodiment 2 |
| Sterilization power | 0.00 | 4.17 | 7.00 |
| Error | 0.00 | 0.37 | 0.00 |

It may be recognized from FIGS. 29A, 29B, Table 5, and Table 6 that Embodiment 1 illustrates 99.99% of sterilization power, and bacteria are not observed in Embodiment 2, so the sterilization is substantially completely achieved.

In other words, the case that the second light is irradiated after the first light is irradiated shows significantly higher sterilization power with the same irradiation amount of light, as compared to the case the first light is irradiated after the second light is irradiated, which means that the same sterilization power is obtained with a smaller amount of light as compared to the case the first light is irradiated after the second light is irradiated. The application of a smaller amount of light means the reduction in the light irradiation time. Accordingly, Embodiment 2 is more reduced in the light irradiation time than Embodiment 1.

Experimental Example 4—Setting Condition of Amount of Light (In Vitro)

The number of bacteria and the sterilization power were measured as function of an amount of light in vitro condition when the first light and the second light are sequentially irradiated, to find out the optimal amount of each light, based on that the sequential irradiation of the first light and the second light shows the increase in the sterilization power.

In the present test, an MRSA strain was used as a pathogen. After the MRSA strain was cultured, a suspension having a constant bacteria concentration (7 log) was prepared. The first light and the second light were sequentially irradiated to the bacteria suspension by changing the dose of the first light to 30 J/cm$^2$, 60 J/cm$^2$, 90 J/cm$^2$, and 120 J/cm$^2$. However, in the case of the second light, the light of 275 nm was employed with a dose limited to 3 mJ/cm$^2$ based on the allowable level of the human body.

Next, the bacteria were diluted at a constant concentration, inoculated into agar plates, and then cultured again. Thereafter, the number of colonies of the cultured bacteria was identified, and the numerical value was converted into a log value.

Each test was performed under the same conditions five times.

Figure 30A:
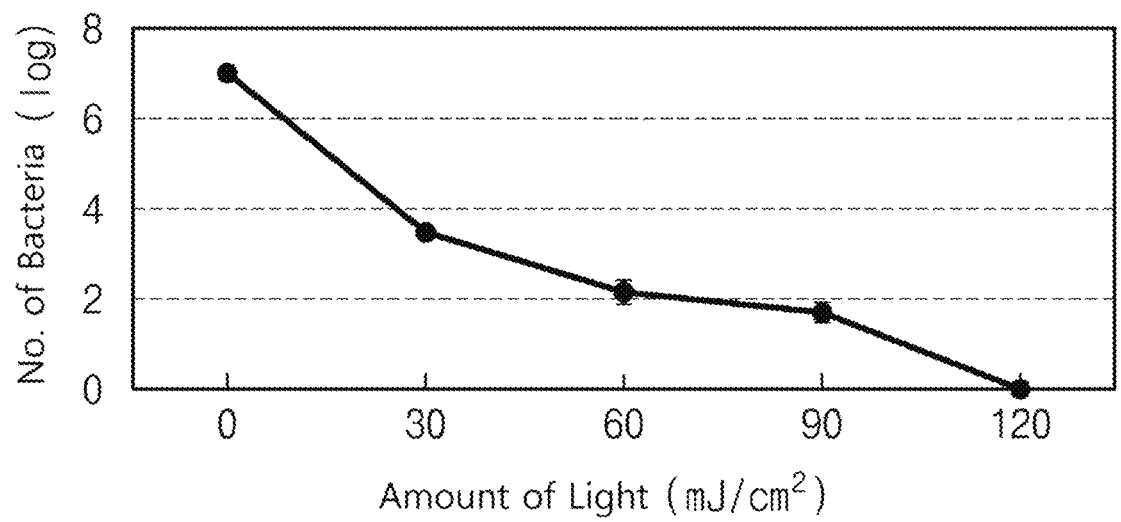
FIG. 30A illustrates the number of bacteria as a function of an amount of the first light under in vitro condition when first light and second light were sequentially irradiated.
Figure 30B:
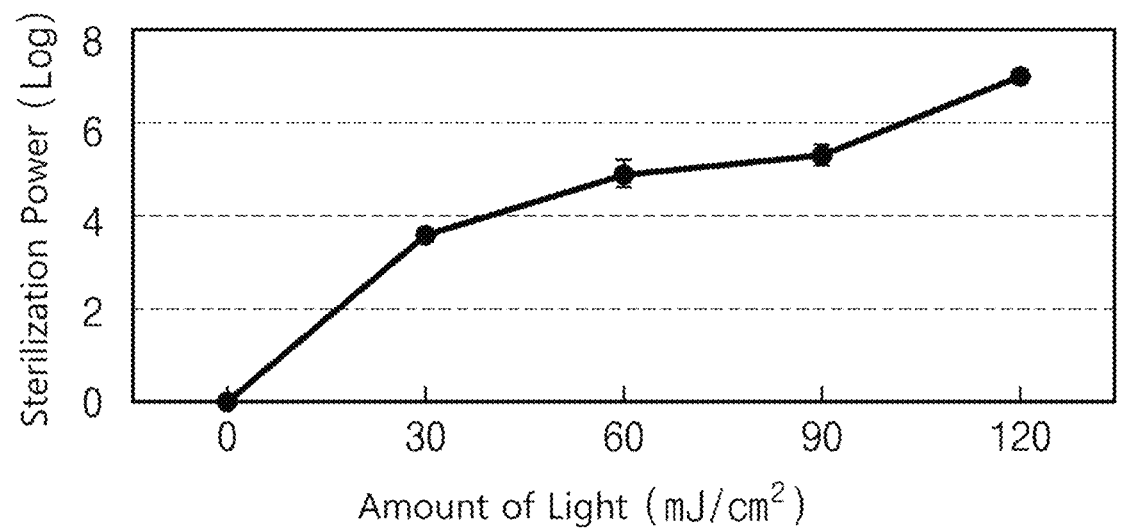
FIG. 30B illustrates sterilization power as a function of the amount of the first light under in vitro condition when the first light and the second light were sequentially.

FIG. 30A and Table 7 show the number of bacteria when an amount of the first light is variously set while the first light and the second light are sequentially irradiated, and FIG. 30B and Table 8 show the sterilization power when an amount of the first light is variously set while the first light and the second light are sequentially irradiated.

TABLE 7

| | Light amount (J/cm$^2$) | | | | |
|---|---|---|---|---|---|
| | 0 | 30 | 60 | 90 | 120 |
| The number of bacteria | 7.00 | 3.47 | 2.13 | 1.70 | 0.00 |
| Error | 0.00 | 0.13 | 0.27 | 0.22 | 0.00 |

TABLE 8

| | Light amount (J/cm$^2$) | | | | |
|---|---|---|---|---|---|
| | 0 | 30 | 60 | 90 | 120 |
| Sterilization power | 0.00 | 3.53 | 4.87 | 5.03 | 7.00 |
| Error | 0.00 | 0.13 | 0.27 | 0.22 | 0.00 |

It may be recognized from FIGS. 30A, 30B, Table 7, and Table 8 that the number of bacteria is reduced as an amount of the first light is increased and the sterilized is completely achieved with a dose of 120 J/cm$^2$.

Experimental Example 5—Setting of Light Amount Condition (In Vivo)

It was recognized through Embodiment 4 that the sterilization is completely achieved when a dose of the first light (having the wavelength of 275 nm) is 120 J/cm$^2$, under the condition that the dose of the second light (having the wavelength of 405 nm) is 3 mJ/cm$^2$. Accordingly, the test was performed to determine whether the above sterilization effect is obtained under in vivo condition.

The present test was performed using a mouse to determine whether the application of light is effective and safe under in vivo condition. The condition for an amount of light is set to the same condition as that in vitro. For the mouse, a BALB/c mouse (6-8 weeks old) was used, the back of the mouse was shaved, and then a cut was formed in the diameter of 10 mm in the back of the mouse. After the pathogenic bacteria was inoculated (at 5 log) on the wound, the first light and the second light were sequentially irradiated by changing the dose of the first light to 30 J/cm², 60 J/cm2, 90 J/cm2, and 120 J/cm2. However, in the case of the second light, the light of 275 nm was employed with a dose limited to 3 mJ/cm² based on the allowable level of the human body. Next, tissues were sampled, and the sampled tissues were disrupted, diluted at a predetermined concentration, inoculated on agar plates, and then cultured again. Thereafter, the number of colonies of the cultured bacteria was identified, and the numerical value was converted into a log value.

Each test was performed under the same conditions five times.

Figure 31A:
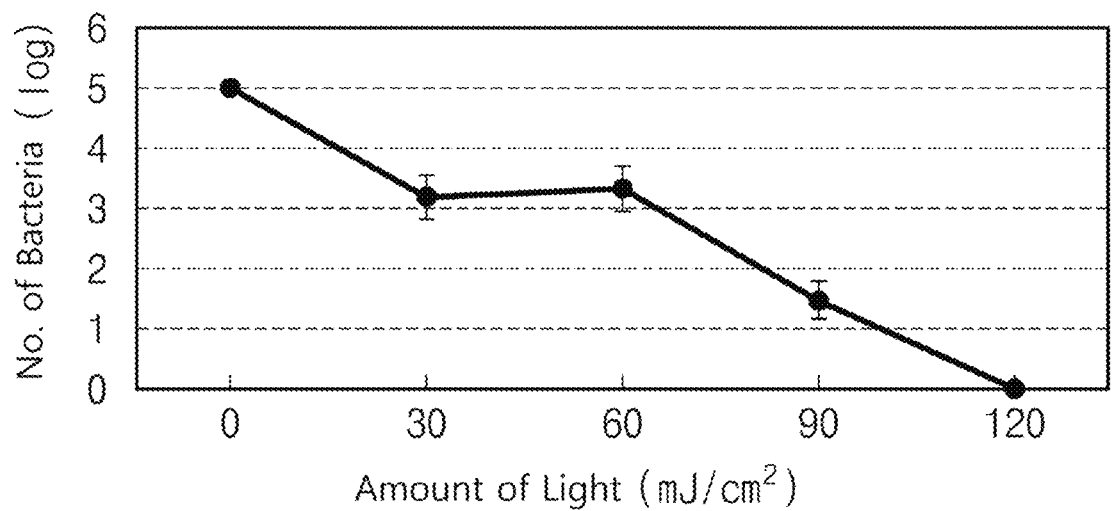
FIG. 31A illustrates the number of bacteria as a function of an amount of the first light under in vivo condition, when first light and second light were sequentially irradiated.
Figure 31B:
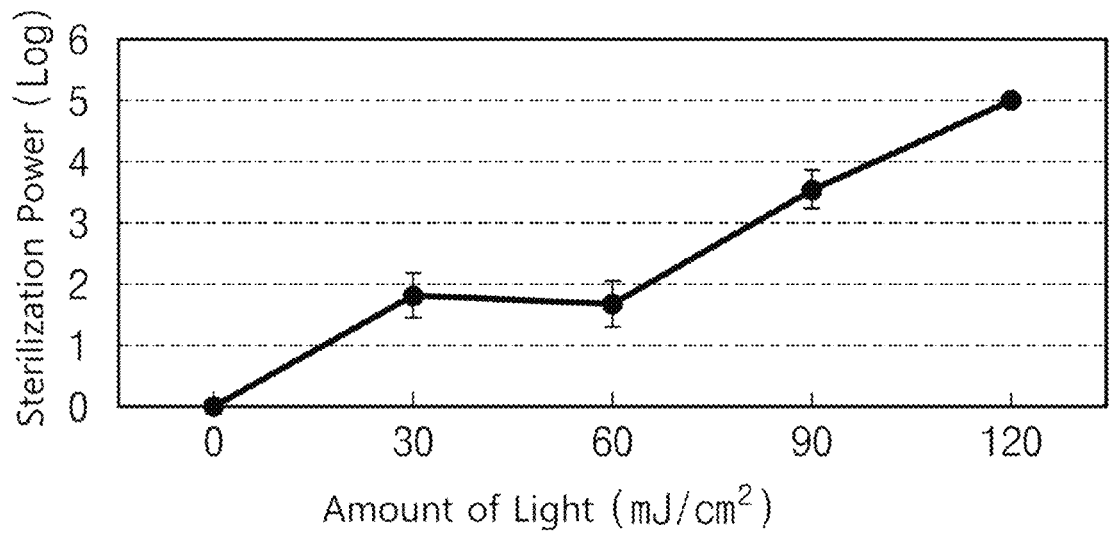
FIG. 31B illustrates the sterilization power as a function of an amount of the first light under in vivo condition, when the first light and the second light were sequentially irradiated.

FIG. 31A and Table 9 show the number of bacteria as a function of an amount of the first light, when the first light and the second light were sequentially irradiated. FIG. 31B and Table 10 show the sterilization power as a function of an amount of the first light, when the first light and the second light were sequentially irradiated.

TABLE 9

|  | Light amount (J/cm²) | | | | |
| --- | --- | --- | --- | --- | --- |
|  | 0 | 30 | 60 | 90 | 120 |
| The number of bacteria | 5.00 | 3.17 | 3.32 | 1.48 | 0.00 |
| Error | 0.00 | 0.36 | 0.38 | 0.31 | 0.00 |

TABLE 10

|  | Light amount (J/cm²) | | | | |
| --- | --- | --- | --- | --- | --- |
|  | 0 | 30 | 60 | 90 | 120 |
| Sterilization power | 0.00 | 1.83 | 1.68 | 3.52 | 5.00 |
| Error | 0.00 | 0.36 | 0.38 | 0.31 | 0.00 |

It may be recognized from FIGS. 31A, 31B, Table 9, and Table 10 that the number of bacteria is reduced as an amount of the first light is increased under in vivo condition and the sterilized is completely achieved with a dose of 120 J/cm².

Experimental Example 6—Effectiveness Evaluation 1 (In Vivo)

In Embodiment 5, a dose of light for sterilization was recognized under in vivo condition, and the variation in the sterilization power and the variation in the number of bacteria as functions of time were tested under in vivo condition.

The present test was performed using a mouse. For the mouse, a BALB/c mouse (6-8 weeks old) was used, the back of the mouse was shaved, and then a cut was formed in the diameter of 10 mm in the back of the mouse. After the pathogenic bacteria was inoculated (at 5 log) on the wound, the first light and the second light were sequentially irradiated and repeatedly irradiated six times in total at the same time every day while a dose of the first light (having the wavelength of 405 nm) is 120 J/cm². In the case of the second light, the light of 275 nm was employed with a dose limited to 3 mJ/cm² based on the allowable level of the human body.

Next, to determine the number of bacteria every day, tissues were sampled, and the sampled tissues were disrupted, diluted at a predetermined concentration, inoculated on agar plates, and then cultured again. Thereafter, the number of colonies of the cultured bacteria was identified, and the numerical value was converted into a log value. To determine the initial sterilization power, the number of bacteria was detected until three-time light irradiation.

Figure 32:
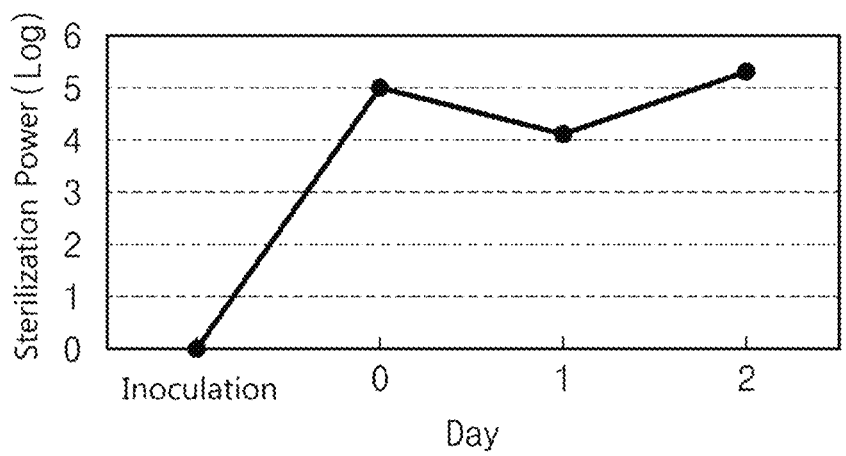
FIG. 32 is a graph illustrating the variation in sterilization power based on days under in vivo condition.
Figure 33:
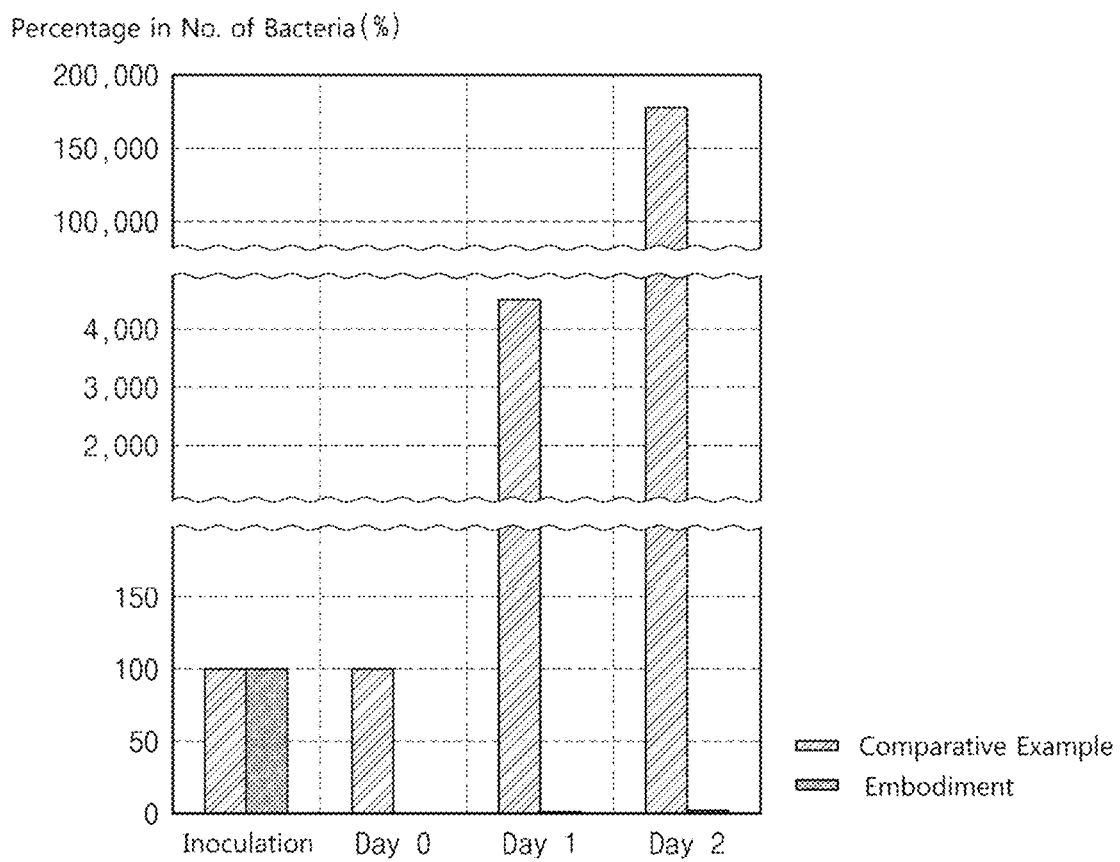
FIG. 33 is a graph illustrating the measurement result of the number of the bacteria based on days under in vivo condition.

FIG. 32 and Table 11 show the variation in the sterilization power depending on days under in vivo condition, and FIG. 33 and Table 12 show the measurement result of the number of bacteria in each day under in vivo condition. In FIG. 33 and Table 12, Comparative example is a non-irradiation group without light irradiation, and Embodiment corresponds to a light irradiation group irradiated with light.

TABLE 11

| Day | Inoculation | 0 | 1 | 2 |
| --- | --- | --- | --- | --- |
| Sterilization power | 0.00 | 5.00 | 4.09 | 5.29 |
| Error | 0.00 | 0.00 | 0.13 | 0.09 |

TABLE 12

|  | The number of bacteria (%) | | | | The number of bacteria (log) | | | |
| --- | --- | --- | --- | --- | --- | --- | --- | --- |
|  | Day | | | | | | | |
|  | Inoculation | 0 | 1 | 2 | Inoculation | 0 | 1 | 2 |
| Non-irradiation group | 100 | 100 | 4,466 | 173,780 | 5.00 | 5.00 | 6.65 | 8.24 |
| Light irradiation group | 100 | 0 | 0.36 | 0.89 | 5.00 | 0.00 | 2.56 | 2.95 |

It may be recognized from FIG. 32, FIG. 33, Table 11, and Table 12 that the sterilization power is continuously maintained to 99.99% or more after light is irradiated to the wound at the initial stage, and the number of bacteria is substantially approximate to '0' when the light is irradiated.

Experimental Example 7—Effectiveness Evaluation 2 (In Vivo)

In Embodiment 5, a dose of light for sterilization was recognized under in vivo condition, and the effect of curing the wound by irradiating the light was tested under in vivo condition based on the dose of light for sterilization.

The present test was performed using a mouse. For the mouse, a BALB/c mouse (6-8 weeks old) was used, the back of the mouse was shaved, and then a wound was formed in the diameter of 10 mm in the back of the mouse. After the pathogenic bacteria was inoculated (at 5 log) on the wound, the first light and the second light were sequentially irradiated and repeatedly irradiated six times in total at the same time every day while a dose of the first light (having the wavelength of 405 nm) is 120 J/cm². However, in the case of the second light, the light of 275 nm was employed with a dose limited to 3 mJ/cm² based on the allowable level of the human body.

The variation in the shape (especially, an area) of the wound was observed at the same time every day. The size of the wound was observed every day till epithelialization, and the value thereof was recorded.

Figure 34:
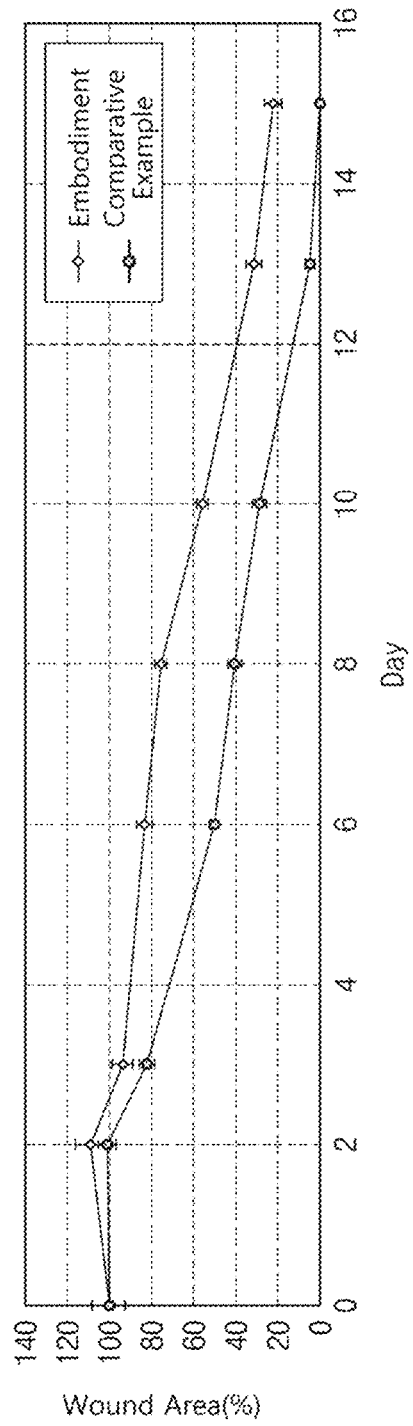
FIG. 34 is a graph illustrating the variation in an area of a wound based on days under in vivo condition.
Figure 35A:
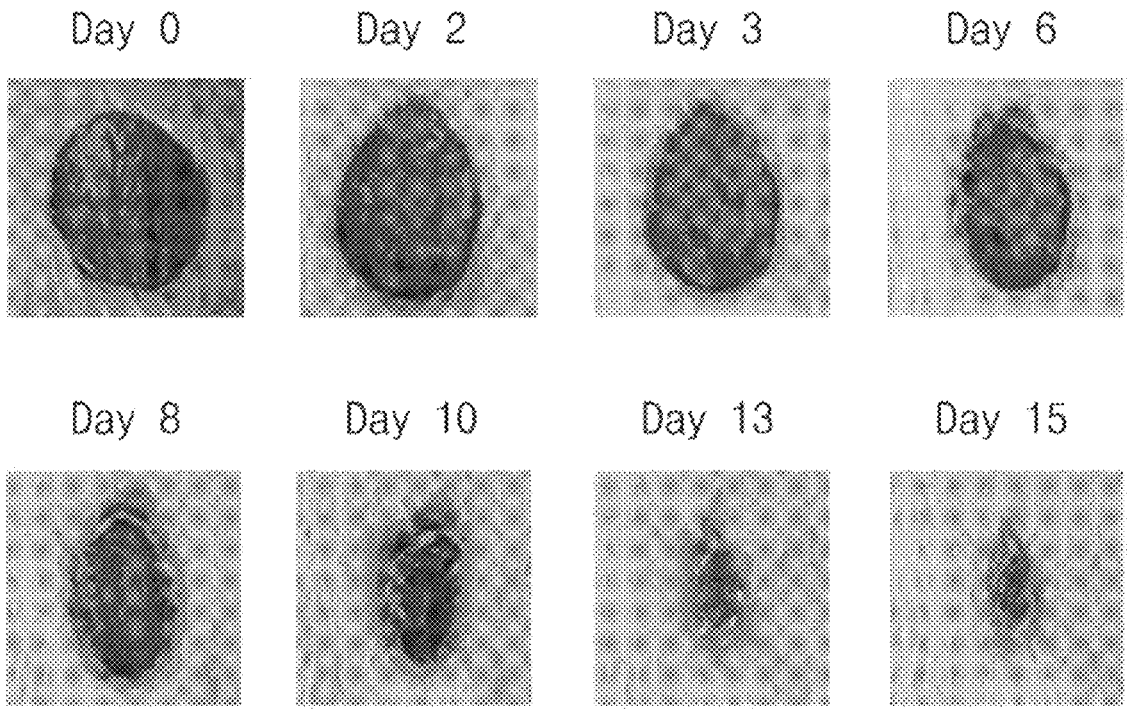
Figure 35B:
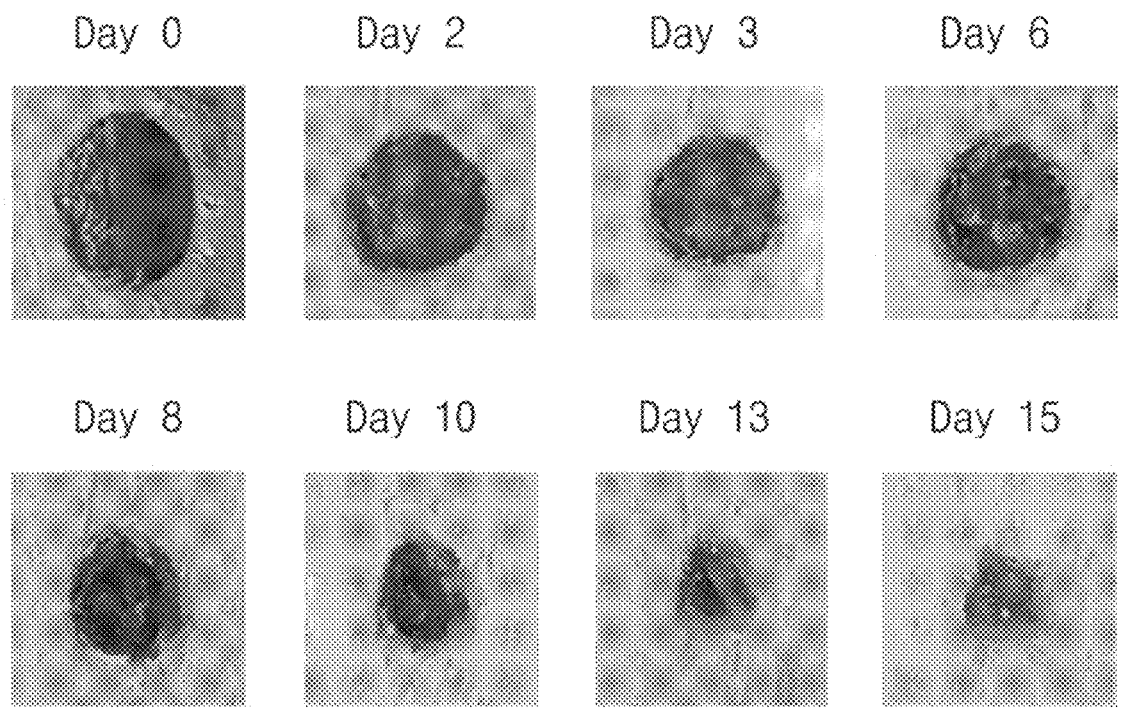

FIG. 34 and Table 13 show the variation in the area of a wound depending on days under in vivo condition. In FIG. 34 and Table 13, Comparative example is a non-irradiation group without light irradiation, and Embodiment corresponds to a light irradiation group irradiated with light. FIGS. 35A and 35B are photographs obtained by capturing images of the shape of the wound area depending on days. FIG. 35A illustrates photographs of a wound in the non-irradiation group, and FIG. 35B illustrates photographs of wounds in the light irradiation group.

TABLE 13

| | Day | | | | | | |
|---|---|---|---|---|---|---|---|
| | Inoculation | 0 | 2 | 3 | 6 | 10 | 15 |
| Non-irradiation group | 100.0 | 100.0 | 108.8 | 93.8 | 83.3 | 55.9 | 22.4 |
| Error | 7.8 | 7.8 | 7.0 | 5.0 | 3.8 | 2.7 | 4.2 |
| Light irradiation group | 100.0 | 100.0 | 101.0 | 82.1 | 50.3 | 28.8 | 0.0 |
| Error | 7.8 | 7.8 | 4.1 | 3.6 | 1.9 | 3.2 | 0.0 |

Referring to FIG. 34, table 15, FIG. 35A, and FIG. 35B, the wound cured was not visibly observed until 2 days from the wound, and the number of bacteria in the wound was significantly reduced. Accordingly, it was determined that the sterilization was in progress. A scab was produced from 2 days after the wound and then the area of the wound was gradually reduced. Accordingly, the curing of the wound is in progress from 2 days after the wound. When the scab was produced on the wound, the wound exposed to the outside was disappeared by the scab. Therefore, the additional infection is less caused. However, the size of the scab and the recovery rate of the wound were greatly varied depending on the sterilization state until the scab was formed. Although the light irradiation group required 6 days till a time point at which the area of the wound was reduced to 50% in the stage of curing the wound, the non-irradiation group required 10 days till the same time point. Further, the epithelialization was achieved on the 15$^{th}$ day in the case of the light irradiation group, and not achieved in the case of the non-irradiation group. Accordingly, according to an embodiment of the present disclosure, it may be recognized that the effect of curing the wound is significantly produced when light is irradiated.

Experimental Example 8—Safety Evaluation 1 (In Vivo)

In the above-described experimental example, a DNA mutation state was determined to determine whether the irradiation condition is harmful to the human body.

In the present test, to determine whether the DNA mutation was caused to the tissue which is not infected through light irradiation, the formation degree of a thymine dimer was determined through immunohistochemical analysis. When an excessive amount of UV is irradiated to the DNA, the DNA mutation such as the thymine dimer is caused, so the cell is destroyed. Accordingly, the DNA mutation may be determined based on the formation degree of the thymine dimer.

The present test was performed using a mouse. For the mouse, a BALB/c mouse (6-8 weeks old) was used, the back of the mouse was shaved, and then a wound is formed in the diameter of 10 mm in the back of the mouse by using the punch. After light was irradiated on the wound, the tissue was sampled, the sampled tissue was fixed through formalin and paraffin, and a cut-out fragment was taken. When light was irradiated, the control group was a non-irradiation group in which light was not treated, Experimental group 1 was a light irradiation group in which an excessive amount of UVC was treated, Experimental group 2 was a light irradiation group in which the first light and the second light were sequentially irradiated in the state that a dose of the first light (having the wavelength of 405 nm) is limited to 120 J/cm² and, a dose of the second light (having the wavelength of 275 nm) is limited to 3 mJ/cm².

Figure 36A:
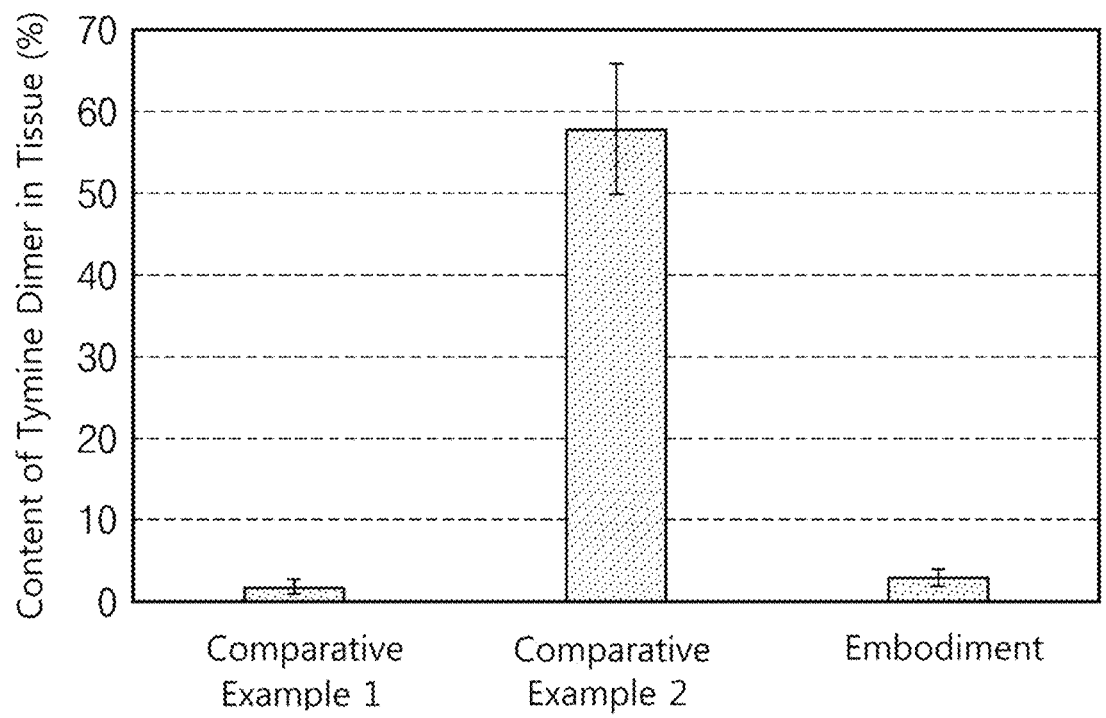
FIG. 36A is a graph illustrating the percentage of a thymine dimer in a tissue.

FIG. 36A and Table 16 illustrate the percentage of a thymine dimer in a tissue. Referring to FIG. 36A and Table 14, although the thymine dimer was found in Experimental group 1, the thymine dimer was not found in Experimental group 2. Accordingly, under the light condition applied according to an embodiment of the present disclosure, it was determined that the DNA mutation was not found even if the light was irradiated to a tissue which was not infected.

TABLE 14

| | Control group | Experimental group 1 | Experimental group 1 |
|---|---|---|---|
| Content (%) | 2 | 58 | 3 |
| Error | 1 | 8 | 1 |

Experimental Example 9—Safety Evaluation 2 (In Vivo)

In the above-described experimental example, the generation state of ROS was determined to determine whether the irradiation condition was harmful to the human body.

The present test is to determine whether the ROS was induced even in the tissue, which was not infected, through light irradiation. When the sterilizing light was irradiated to the infectious bacteria, the ROS was induced to destroy the bacteria.

The present test was performed using a mouse. For the mouse, a BALB/c mouse (6-8 weeks old) was used, the back of the mouse was shaved, and then a wound is formed in the diameter of 10 mm in the back of the mouse by using the punch. After the light was irradiated on the wound, a Dichlorofluorescin diacetate (DCFH-DA) was treated for a part irradiated with light and a light emission was measured with respect to a part stained with DCFH-DA, so it was determined that the ROS was present. DCFH-DA was oxidized by the ROS in the cell to emit fluorescent light. When DCFH-DA was excited, the absorption wavelength was in the range of 445 nm to 490 nm, and the fluorescent wavelength was in the range of 515 nm to 575 nm.

In this case, the control group was a non-treatment group in which non-treatment is added, Experimental group 1 was a group treated with hydrogen peroxide, and Experimental group 2 was a treatment group to which the first light and the second light are sequentially irradiated in the state that a dose of the first light (having the wavelength of 405 nm) is limited to 120 J/cm$^2$, and a dose of the second light (having the wavelength of 275 nm) is limited to 3 mJ/cm$^2$.

Figure 36B:
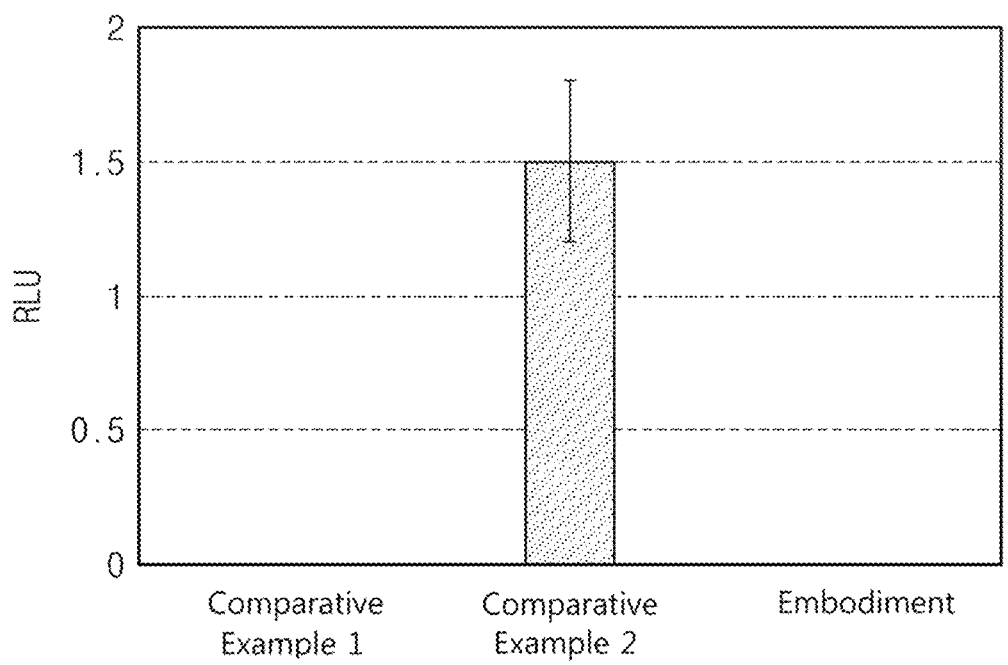
FIG. 36B illustrates a light emission degree of a part stained with DCFH-DA.

FIG. 36B and Table 15 illustrate the light emission degree of a part stained with DCFH-DA. Referring to FIG. 36B and table 157, fluorescent is emitted in Experimental group 2 and Experimental group 1, so it is determined that ROS is present. However, since fluorescent is not absent in Experiment group 2, so it is determined that ROS is absent. Accordingly, under the light condition applied according to an embodiment of the present disclosure, it was determined that the ROS was not produced even if the light was irradiated to a tissue which was not infected.

TABLE 15

|  | Control group | Experimental group 1 | Experimental group 2 |
|---|---|---|---|
| Light emission degree (RLU; Relative Light Units) | 0 | 1.5 | 0 |
| Error | 0 | 0.3 | 0 |

Experimental Example 13—Sterilization Power Test in Supplying Oxygen

In the present experiment, sterilization power was tested depending on whether oxygen is additionally supplied when the first light is irradiated. In the present experimental example, the used strain was *Staphylococcus aureus*, a bacteria suspension was irradiated with the first light of a 405 nm wavelength and the contact count with air (that is, the contact with oxygen) was increased by using the stirrer. The initial concentration of the bacteria suspension was 1×10$^6$ CFU/mL, and the first light source was disposed at a predetermined height from a plate having the bacteria suspension and irradiated the first light. The suspension irradiated with the first light was diluted to a specific concentration, inoculated into agar plates, and then cultured again. Thereafter, the number of colonies of the cultured bacteria was identified, and the numerical value thereof was converted into a log value, thereby measuring the sterilization power.

FIG. 37 and Table 16 show the sterilization power based on an amount of the first light and the P-value thereof which were measured.

TABLE 16

|  |  | Amount of light (J/cm$^2$) | | | | |
|---|---|---|---|---|---|---|
|  |  | 0 | 30 | 60 | 90 | 120 |
| Without Oxygen | Sterilization Power | 0.00 | 0.44 | 0.86 | 0.98 | 1.15 |
|  | Error | 0.00 | 0.22 | 0.48 | 0.42 | 0.40 |
| With Oxygen | Sterilization Power | 0.00 | 1.24 | 2.06 | 2.94 | 3.64 |
|  | Error | 0.00 | 0.34 | 0.36 | 0.47 | 0.62 |
|  | P-value | — | 0.0225 | 0.0304 | 0.0083 | 0.0055 |

Referring to FIG. 37 and Table 16, it can be understood that the sterilization power is significantly increased, when oxygen is continuously supplied by increasing the contact time with the air and the contact count with the air by using the stirrer.

Although an exemplary embodiment of the present disclosure has been described for illustrative purposes, those skilled in the art will appreciate that various modifications, and substitutions are possible, without departing from the scope and spirit of the invention as disclosed in the accompanying claims. Accordingly, the technical scope of the present disclosure is not limited to the detailed description of this specification, but should be defined by the claims.

We claim:

1. A dressing for applying to a wound of a patient, the dressing comprising:
   a dressing body to make contact with a wound of a patient, wherein the dressing body has a first surface to make contact with the wound of the patient and a second surface opposite to the first surface; and
   a light irradiation device to apply light to the wound of the patient for sterilization and preventing infection and including:
   a device board having at least one light emitting diode mounted thereon, the at least one light emitting diode arranged to be on the first surface of the dressing body and in direct contact with the first surface of the dressing body and configured to apply the light toward the wound;
   wherein the light has a predetermined range of wavelength bands among an infrared light wavelength, a visible light wavelength, and an ultraviolet light wavelength such that application of the light induces destruction of bacteria present in the wound of the patient or accelerates a recovery of the wound; and
   wherein the light irradiation device includes:
   first and second light sources operable to emit first light and second light at timings close to each other, regardless of whether the timings overlap or not, the first light and the second light having mutually different wavelengths, respectively,
   wherein the first light has a first wavelength band for inducing the destruction of the bacteria by damaging a cell of the bacteria, as the first light acts on a photosensitizer present in the bacteria, and
   the second light has a second wavelength band for inducing the destruction of the bacteria by changing a structure of a genetic material present in the cell of the bacteria.

2. The dressing of claim 1, wherein the first light is blue light, and the second light is ultraviolet light, and wherein the second light is irradiated with a daily maximum irradiation amount of about 3 mJ/cm$^2$.

3. The dressing of claim 2, wherein the first light has a wavelength in a range of about 400 nm to about 420 nm, or a range of about 455 nm to about 470 nm.

4. The dressing of claim 1, further comprising: a controller to control the first light and the second light.

5. The dressing of claim 4, further comprising:
   an oxygenator connected with the controller to supply oxygen.

6. The dressing of claim 1, wherein the first light is irradiated for a first time, and the second light is irradiated for a second time shorter than the first time.

7. The dressing of claim 6, wherein irradiation of the second light starts after irradiation of the first light is completed.

8. The dressing of claim 6, wherein irradiation of the second light starts before irradiation of the first light is completed, and at least a portion of the first time and at least a portion of the second time mutually overlap.

9. The dressing of claim 1, wherein the light irradiation device further includes:
a water-proof protective film provided on the at least one light emitting diode to protect the light emitting diode.

10. The dressing of claim 9, wherein the device board is flexible.

11. (The dressing of claim 1, further comprising:
a drape provided in the dressing body and attached to a skin close to the wound of a patient to form an inner space by covering the wound;
a negative pressure generating member to apply negative pressure to the inner space by communicating with the inner space; and
a tube that connects the inner space with the negative pressure generating member.

12. The dressing of claim 11, further comprising:
a pressure sensor provided in the inner space to sense whether the negative pressure is applied to the inner space, wherein the pressure sensor is provided on the device board.

13. The dressing of claim 12, wherein the dressing body has:
a first thickness when the negative pressure is not applied, and a second thickness when the negative pressure is applied, and
wherein the light emitting diode is exposed from the device board toward the wound to correspond to the second thickness when the negative pressure is applied.

14. The dressing of claim 11, wherein the dressing body has an exudate opening to absorb exudate from the wound.

15. The dressing of claim 1, wherein the light irradiation device further includes a light emitting diode provided in a form of a flip chip having first and second electrodes, and wherein the first and second electrodes of the flip chip are directly connected with a wiring of a device board.

16. The dressing of claim 1, wherein the dressing body is at least one of a foam dressing type, a hydrocolloid dressing type, a porous silicone film dressing type, or a hydrofiber dressing type.

17. The dressing of claim 1, further comprising: a sensor unit provided inside or outside the dressing body to sense a state of the wound of the patient.

18. The dressing of claim 17, wherein the light irradiation device interworks with the sensor unit to set a wavelength and an output intensity of light emitted from the light emitting diode.

19. The dressing of claim 1, wherein the light irradiation device emits light having a wavelength band that varies depending on a phase of the wound of the patient.

20. The dressing of claim 19, wherein the light irradiation device is operable to emit:
light having a blue wavelength band, when the phase of the wound of the patient is an infection phase,
light having a green wavelength band or a first red wavelength band, when the phase of the wound of the patient is a proliferation phase, or
light having a second red wavelength band or an infrared wavelength band, when the phase of the wound of the patient is a maturation phase.

* * * * *